(12) United States Patent
Cabon et al.

(10) Patent No.: US 8,765,705 B2
(45) Date of Patent: Jul. 1, 2014

(54) OLIGONUCLEOTIDES INHIBITING CELLULAR MIGRATION

(75) Inventors: Florence Cabon, Vitry (FR); Virginie Firlej, Kremlin Bicetre (FR); Catherine Gallou-Kabani, Gif-sur-Yvette (FR); Natalia Prevarskaya, Rumegies (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/387,829

(22) PCT Filed: Jul. 30, 2010

(86) PCT No.: PCT/EP2010/061156
§ 371 (c)(1),
(2), (4) Date: Apr. 6, 2012

(87) PCT Pub. No.: WO2011/012716
PCT Pub. Date: Feb. 3, 2011

(65) Prior Publication Data
US 2012/0195890 A1 Aug. 2, 2012

(30) Foreign Application Priority Data
Jul. 31, 2009 (EP) .................................... 09305723

(51) Int. Cl.
*C12N 15/11* (2006.01)
(52) U.S. Cl.
USPC ...................................................... 514/44 A
(58) Field of Classification Search
USPC ...................................................... 514/44 A
See application file for complete search history.

(56) References Cited

U.S. PATENT DOCUMENTS

2010/0292316 A1* 11/2010 Sanders et al. ................ 514/458

FOREIGN PATENT DOCUMENTS

WO 2006/010492 2/2006

OTHER PUBLICATIONS

Carlson et al, Structures of Thrombospondins:, Cell Mol Life Sci, Mar. 2008, pp. 674-686, 65 (5).
Good et al., "A Tumor Suppressor-Dependent Inhibitor of Angiogenesis is Immunologically and Functionally Indistinguishable From a Fragment of Thrombospondin", Proc Nati Acad Sci, Sep. 1990, pp. 6624-6628, vol. 87.
Jimenez et al., "Signals Leading to Apoptosis-Dependent Inhibition of Neovascularization by Thrombospondin-1", Nature Medicine, Jan. 2000, pp. 41-48, vol. 6, No. 1.
Ren et al., "Regulation of Tumor Angiogenesis by Thrombospondin-1",Biochimica et Biophysica Acta, 2006, pp. 178-188, 1765.
Zhang et al., "Thrombospondin-based Antiangiogenic Therapy", Microvasc Res, 2007, pp. 90-99, 74(2-3).
Colombel et al., "Androgens Repress the Expression of the Angiogenesis Inhibitor Thrombospondin-1 in Normal and Neoplastic Prostate", Cancer Res, 2005, pp. 300-308, 65.
Fontana et al., "Human Breast Tumors Override the Antiangiogenic Effect of Stromal Thrombospondin-1 In Vivo", Int J Cancer, 2005, pp. 686-691, 116.
Adams, J. et al., "Functions of the Conserved Thrombospondin Carboxy-Terminal Cassette in Cell-Extracellular Matrix Interactions and Signaling", The International Journal of Biochemistry & Cell Biology, 2004, pp. 1102-1114, 36.
Abeele et al., Bcl-2-Dependent Modulation of Ca2+ Homeostasis and Store-Operated Channels in Prostate Cancer Cells, Cancer Cell, Mar. 2002, pp. 169-179, vol. 1.
Lehen'Kyi et al., "TRPV6 Channel Controls Prostate Cancer Cell Proliferation Via Ca2+/NFAT-Dependent Pathways", Oncogene, 2007, pp. 7380-7385, 26.
Thebault et al., "Differential Role of Transient Receptor Potential Channels in Ca 2+ Entry and Proliferation of Prostate Cancer Epithelial Cells", Cancer Res, 2006, pp. 2038-2047, 66.
Carthew et al., "Origins and Mechanisms of miRNAs and siRNAs", Cell, Feb. 2009, pp. 642-655, 136 (4).
Prevarskaya et al., "TRP Channels in Cancer", Biochimica et Biophysica Acta, 2007, pp. 937-946, 1772.
International Search Report dated Dec. 212, 2010, in PCT/EP2010/061156.
Karen et al., "The Effect of Thrombospondin-L on Breast Cancer Metastasis" Breast Cancer Research and Treatment, Apr. 2008, pp. 85-96, vol. 114, No. 1, Kluwer Academic Publishers, BO, XP019671367.
Kang et al., "Inhibition of Trichostatin A-induced Antianglogenesis by Small-Interfering RNA for Thrombospondin-I", Experimental & Molecular Medicine, Jun. 2007, pp. 402-411, vol. 39, No. 3, XP002572637.
De Fraipont et al., "Thrombospondins and Tumor Angiogenesis" Trends in Molecular Medicine, Sep. 2001, pp. 401-407, vol. 7, No. 9, XP002572638.
Roberts, D., "Thrombospondins: from Structure to Therapeutics", Cell Mol Life Sci, Mar. 2008, pp. 669-671, 65(5).

* cited by examiner

*Primary Examiner* — Brian Whiteman
(74) *Attorney, Agent, or Firm* — Young & Thompson

(57) ABSTRACT

Oligonucleotides inhibiting cellular migration, and the use of at least one inhibitor of protein expression, which inhibits the expression of TSP1 protein, or a protein, which controls the expression of TSP1 or mediates the activity of TSP1, or one inhibitor of protein activity, this inhibitor inhibiting the activity of the TSP1 protein, in particular the activity responsible for the stimulation of cell migration, or one protein which controls the expression or mediates the activity of TSP1 for the manufacture of a drug for the prevention or the treatment of primary tumors or invasive or metastatic tumors.

18 Claims, 9 Drawing Sheets

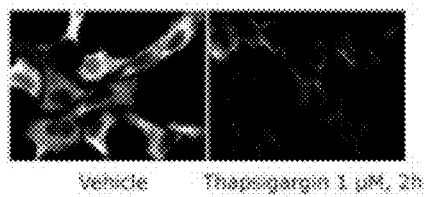
Fig 2A
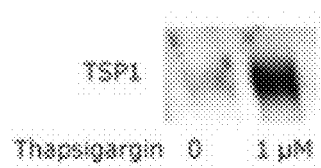
Fig 2B
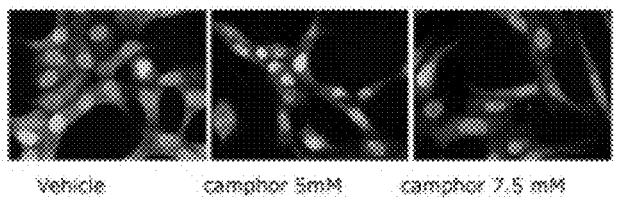
Fig 2C
Fig 2D
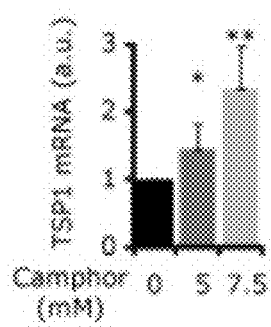
Fig 2E
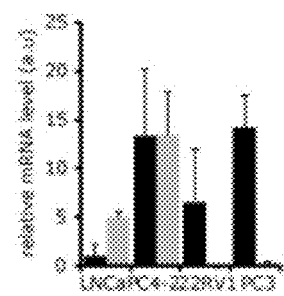
Fig 2F
Fig 2G
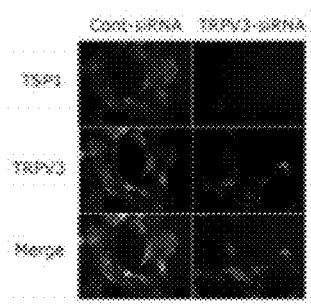
Fig 2H
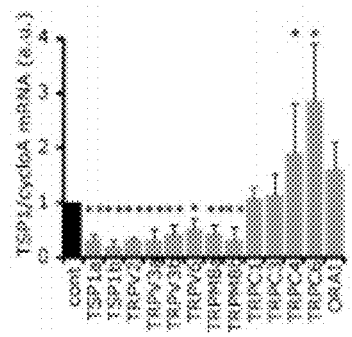
Fig 2I
Fig 2J

OLIGONUCLEOTIDES INHIBITING CELLULAR MIGRATION

The present invention relates to oligonucleotides inhibiting cellular migration, invasion or metastasis.

In particular, it relates to the use of double-stranded oligonucleotides for the manufacture of drug for the prevention or treatment of human pathologies, such as tumors.

More particularly, the invention aims at inhibiting the expression of genes, the products of which participate in triggering or maintaining pathological states.

The invention also relates to the pharmaceutical compositions for the inhibition of the expression of genes, the products of which participate in triggering or maintaining pathological states.

Thrombospondin-1 (TSP1) is a large ~450 kDa-trimeric calcium-binding molecule composed of several domains (Carlson et al., 2008) which binds to numerous ligands and receptors, including several integrins and the scavenger receptor CD36. TSP1, which was the first antiangiogenic molecule characterized (Good et al., 1990), inhibits In vitro the migration and induces the apoptosis of endothelial cells (Jimenez et al., 2000). TSP1 expression is inhibited in a large number of tumors (Ren et al., 2006; Zhang and Lawler, 2007) including primary breast tumors and androgen-dependent prostate tumors, where there is an inverse correlation between TSP1 expression and the blood vessel density (MVD) (Colombel et al., 2005; Fontana et al., 2005b). It has been previously reported that the TSP1 expression is high, and no longer associated with a reduced MVD, both in breast metastases (Fontana et al., 2005a), and in invasive or metastatic prostate tumors that became refractory to hormonal ablation (Colombel et al., 2005). However, a functional involvement of TSP1 in tumor development has not been established.

It is now well established that calcium, which binds to the type III repeats of TSP1 and modifies its folding and properties (Adams, 2004; Carlson et al., 2008), regulates the proliferation, differentiation and apoptosis of cancer cells (Abeele et al., 2002; Lehen'Kyi et al., 2007; Thebault et al., 2006). Indeed, the cyclic morphological and adherence changes observed during cell migration are accompanied by repetitive changes in $[Ca^{2+}]_i$ depending on $Ca^{2+}$ influx through channels located on the plasma membrane channels. The molecular nature of these channels in migrating cells, and even more so for metastatic cancer cells, is still largely unknown.

RNA interference (RNAi) is a post-transcriptional gene-silencing mechanism where the introduction of double-stranded RNA into a cell inhibits gene expression in a sequence-dependent fashion. RNAi has been observed in a number of organisms such as mammals, drosophila, nematodes, fungi and plants, RNAi can be triggered in mammalian cells, notably by the introduction of synthetic siRNA (Carthew and Sontheimer, 2009)

One of the aims of the invention is to provide inhibitors of molecules which facilitate primary tumor development, or tumor invasion, or metastasis.

Another aim of the present invention is to provide inhibitors of the molecules which control or mediate the activity of the above mentioned molecules.

Another aim of the present invention is to provide pharmaceutical compositions comprising said inhibitors.

Another aim of the present invention is to provide pharmaceutical compositions which are efficient to inhibit both primary tumors and invasive or metastatic tumor progression.

The invention relies on the unexpected experimental results according to which the TSP1 expression stimulates the migration of the tumor cells out of the hypoxic environment and thus its inhibition produces antitumor effects.

Thus, in a general embodiment, the invention relates to the use of at least:
one inhibitor of protein expression, which inhibits the expression of:
  TSP1 protein, or
  a protein, which controls the expression of TSP1 or mediates the activity of TSP1,
or,
one inhibitor of protein activity, said inhibitor inhibiting the activity of:
  the TSP1 protein, in particular the activity responsible for the stimulation of cell migration, or
  one protein which controls the expression or mediates the activity of TSP1, for the manufacture of a drug for the prevention or the treatment of primary tumors, or invasive or metastatic tumors.

Tumors depend on an adequate blood supply for their growth. Therefore, for the man skilled in the art, inhibition of angiogenesis is a method to inhibit tumor development. A number of antiangiogenic compounds have been developed in the past to reach this goal. On the contrary, inhibition of an inhibitor of angiogenesis such as TSP1 should increase blood vessel density, and is thus expected to foster tumor development. Up to now, it could not be encompassed for the man skilled in the art to inhibit the expression or the activity of TSP1 protein to inhibit tumor development.

The inventors have demonstrated here that although inhibition of TSP1 in tumors does increase blood vessels density, TSP1 inhibition results in a strong antitumoral effect.

As tumors expand, hypoxic regions frequently occur in tumors. Hypoxia stimulates the production of angiogenic factors such as Vascular Endothelial Growth Factor (VEGF), which is a strong trigger of angiogenesis. New blood vessels then irrigate the tumor and provide oxygen, thus reducing hypoxia. As hypoxia reduces, VEGF production is no longer stimulated, producing a feed back mechanism.

No such feed back mechanism occurs to control TSP1 production in tumors: the inventors have shown here that hypoxia induces TSP1 which inhibits angiogenesis, and thus increases hypoxia.

The Inventors have also demonstrated here that TSP1 can be induced by a second mechanism: pharmacologic molecules such as camphor or thapsigargin that increase the cytosolic calcium concentration induce TSP1 secretion and/or production. Such an increase in calcium concentration can be produced by a deregulation of calcium channels. The inventors demonstrate that several calcium channels of the Transient Receptor Potential (TRP) family regulate TSP1 expression. Of note, several of these channels were shown to be upregulated in cancer cells (Prevarskaya et al., 2007).

Inductions of TSP1 by hypoxia or by a modification of intracellular calcium concentration are two processes that can occur independently. However, some cross talks may occur between these processes as the inventors show that at least one of TRP channels, TRPV3, is upregulated by hypoxia. In addition, the inventors show that hypoxia induces an increase in the intracellular calcium concentration.

Importantly, the Inventors have also demonstrated that in prostate tumors, TSP1 is a major stimulator of cell migration in vitro and of tumor development in vivo as its silencing strongly inhibited tumor development.

An inhibitor of protein expression refers to a biological molecule, such as an oligonucleotide or a peptide, or a protein, or any other kind of organic or inorganic molecules, which inhibit the transcription of the gene coding said protein, or the translation of the mRNA of the gene coding said protein.

A protein which controls the expression of TSP1 refers to a protein which controls the transcription of TSP1 gene or the translation of TSP1 gene transcript. For instance, several non-voltage dependent cationic channels of the Transient Receptor Potential (TRP) family, such as TRPV2, TRPV3, TRPV6, TRPM8, have been taken into account in the present invention.

A protein which mediates the activity of TSP1 refers to a protein, such as the receptors of TSP1 protein, which could mediate the biological activity of TSP1 protein. For instance, the receptors, CD36 and B3 integrin have been taken into account in the present invention.

An inhibitor of protein activity refers to a biological molecule, such as an oligonucleotide, or a peptide, or a protein, or any other kind of organic or inorganic molecules which inhibit the biological activity of said protein in in vivo or in vitro tests.

The stimulation of cell migration refers to a situation where the percentage of migrating cells in the treated group is statistically higher than that of the control group.

The cell migration capacity can be measured in vitro using a modified Boyden Chamber. Boyden Chamber consists of two compartments separated by a permeable membrane. Cells are placed in the upper chamber and the chemotactic factors in the lower chamber. Cells migrating through the membrane are counted.

A detailed migration assay is given in the example section.

A primary tumor refers to a tumor growing at the anatomical site where tumor progression began and proceeded to yield a cancerous mass.

An invasive tumor refers to a cancer that has broken through its initial limits limiting membrane, such as the capsule of the prostate. This cancer spreads outside the tissue where it initially develops and grows into nearby, healthy tissues. "Invasive" does not imply that the cancer has already spread outside the prostate. "Invasive" has the same meaning as infiltrating.

A metastatic tumor refers to a cancer that has spread from its original site to one or more additional body sites.

In another embodiment, the inhibitor of protein expression inhibits the expression of proteins chosen from the group comprising TSP1, TRPV2, TRPV3, TRPV6, TRPM8, CD36, or B3 integrin.

TRPV2, TRPV3, TRPV6, TRPM8 belong to non-voltage dependent cationic channels of the Transient Receptor Potential (TRP) family. These proteins control the expression of TSP1 protein.

CD36 and B3 integrin are receptors of TSP1. It is known that TSP1 binds to a number of receptors (Roberts, 2008). These receptors can mediate the activity of TSP1 protein.

In another embodiment, the inhibitor of protein expression inhibits the in vivo and in vitro expression of proteins chosen from the group comprising TSP1, TRPV2, TRPV3, CD36, or B3 integrin.

In vivo tests involve living animals, including human, mice and rat. In the present invention, the in vivo inhibition of protein expression can be measured by the growth and the volume of tumoral tissue which is xenografted into nude mice. The reduction of the volume of a tumoral tissue after the injection of the inhibitor of protein expression, or the inhibitor of protein activity, means the in vivo inhibition of said protein expression.

In vitro tests refer, for instance, to the use of cells in culture, or real-time RT-PCT, etc., in order to measure the inhibition of protein expression.

In another embodiment, the inhibitor of protein expression inhibits the in vivo expression of proteins chosen from the group comprising TSP1, TRPV2, TRPV3.

In another embodiment, the inhibitor of the protein expression is a double-stranded oligonucleotide or a single-stranded oligonucleotide.

By the expression "oligonucleotide" is meant a polynucleotide from 2 to 100, and more particularly from 5 to 50, and preferably 13 to 25 nucleotides, and in particular 19, 20, 21 oligonucleotides, of type of ribonucleotides, deoxyribonucleotides or the mix of them.

A double-stranded oligonucleotide can refer to a siRNA. A single-stranded oligonucleotide can refer to a microRNA or any anti-sense single strand oligonucleotide used to inhibit the expression of target gene.

The use of a double-stranded oligonucleotide is more efficient than other previous anti-RNA strategies such as ribozyme or single stranded antisense deoxynucleotides because it cleaves repeatedly its target mRNA.

Furthermore, a double-stranded oligonucleotide is more stable than a single-stranded oligonucleotide.

In another embodiment, the inhibitor of the protein expression is:
  a double-stranded oligonucleotide comprising two oligonucleotide sequences, (a) and (b), forming a hybrid,
  wherein the oligonucleotide sequence (a)
    is either complementary to the oligonucleotide sequence (b),
    or presents less than 40% mismatches with said oligonucleotide sequence (b), and
  wherein the oligonucleotide sequence (a)
    is either complementary to a target sequence belonging to the RNA or DNA molecule coding one of the proteins above-defined, the expression of which is to be inhibited,
    or presents less than 40% mismatches with a target sequence belonging to the RNA or DNA molecule coding one of the proteins above-defined, the expression of which is to be inhibited,
  or a fragment of the above-defined double-stranded oligonucleotides (a) and (b), comprising two complementary fragments of the respective above-defined oligonucleotide sequences (a) and (b), provided that said fragment conserves the property of inhibiting the expression of one of the proteins above-defined.

The oligonucleotide sequence (a) is preferably complementary to the oligonucleotide sequence (b), but can comprise 1-8 mismatches, particularly 5, more particularly 3 mismatches, still more particularly 1 mismatch with the oligonucleotide sequence (b).

The oligonucleotide sequence (a) is preferably complementary to the target sequence, but can comprise 1-8 mismatches, particularly 5, more particularly 3 mismatches, still more particularly 1 mismatch with the target sequence; this application is particular when the length of the target sequence is of 21 nucleotides.

In another embodiment, the inhibitor of the protein expression is:
  a double-stranded oligonucleotide comprising two oligonucleotide sequences, (a) and (b), forming a hybrid,
    wherein each oligonucleotide sequence comprises at one of its 3' or 5' ends, one to five unpaired nucleotides forming single-stranded ends extending beyond the hybrid, wherein the part inside the hybrid of the oligonucleotide sequence (a)
is either complementary to the oligonucleotide sequence (b),
or presents less than 40% mismatches with said oligonucleotide sequence (b), and
wherein the oligonucleotide sequence (a)
is either complementary to a target sequence belonging to the RNA, or DNA molecule coding one of the proteins above-defined, the expression of which is to be inhibited,
or presents less than 40% mismatches with a target sequence belonging to the RNA or DNA molecule coding one of the proteins above-defined, the expression of which is to be inhibited,
or a fragment of the above-defined double-stranded oligonucleotides (a) and (b), comprising two complementary fragments of the respective above-defined oligonucleotide sequences (a) and (b), provided that said fragment conserves the property of inhibiting the expression of one of the proteins above-defined.

The oligonucleotide sequence (a) is preferably complementary to the oligonucleotide sequence (b), but can comprise 1-8 mismatches, particularly 5, more particularly 3 mismatches, still more particularly 1 mismatch with the oligonucleotide sequence (b).

The oligonucleotide sequence (a) is preferably complementary to the target sequence, but can comprise 1-8 mismatches, particularly 5, more particularly 3 mismatches, still more particularly 1 mismatch with the target sequence; this application is particular when the length of the target sequence is of 21 nucleotides.

In an advantageous embodiment, the oligonucleotide sequence complementary to the target sequence comprises from 15 to 25 nucleotides.

The oligonucleotide sequence complementary to the target sequence is an antisense strand, and wherein the second oligonucleotide sequence complementary to the first sequence is a sense strand.

The nature of the nucleotides comprised in the oligonucleotide sequence of the present invention is ribonucleotide, deoxyribonucleotide or both of them.

The nucleotides comprised in the oligonucleotide sequence of the present invention can be natural nucleotides (A, T, G, C, U), or chemically modified nucleotides, or a mix of them, in particular chemically modified nucleotides comprising a reactive group, or a linking agent, such as 5-methylcytidine, xanthinosine pseudouridine, dihydrouridine, inosine, ribothymidine, 7-methylguanosine or Locked Nucleic Acids (LNA).

Preferably, the oligonucleotide sequence complementary to the target sequence, also designed by the antisense strand, comprises substantially natural ribonucleotides and the sense strand, can comprise ribonucleotides, deoxyribonucleotides or both of them.

The above mentioned definition also applies to the pharmaceutical compositions and the oligonucleotides sequences further described.

In an advantageous embodiment, the double-stranded oligonucleotide comprises, at the 3' end of each of the two said oligonucleotide sequences, 1 to 5 nucleotides, preferably 2 to 3 nucleotides, extending beyond the hybrid.

In a more advantageous embodiment, the nucleotides extending beyond the hybrid are deoxythymidines.

In a particular embodiment, the expression of the target sequence represented by SEQ ID NO: 41 (TSP1) is inhibited by the double-stranded oligonucleotide described in the present invention.

In another particular embodiment, the expression of the target sequence represented by SEQ ID NO: 42 (TRPV3) is inhibited by the double-stranded oligonucleotide described in the present invention.

In another particular embodiment, the double-stranded oligonucleotide is chosen from one of the following couples consisting in (SEQ ID NO: 1 and SEQ ID NO: 2); (SEQ ID NO: 3 and SEQ ID NO: 4); (SEQ ID NO: 5 and SEQ ID NO: 6); (SEQ ID NO: 7 and SEQ ID NO: 8); (SEQ ID NO: 9 and SEQ ID NO: 10); (SEQ ID NO: 11 and SEQ ID NO: 12); (SEQ ID NO: 13 and SEQ ID NO: 14); (SEQ ID NO: 15 and SEQ ID NO: 16); (SEQ ID NO: 17 and SEQ ID NO: 18); (SEQ ID NO: 19 and SEQ ID NO: 20); (SEQ ID NO: 21 and SEQ ID NO: 22); (SEQ ID NO: 23 and SEQ ID NO: 24); (SEQ ID NO: 25 and SEQ ID NO: 26); (SEQ ID NO: 27 and SEQ ID NO: 28); (SEQ ID NO: 29 and SEQ ID NO: 30); (SEQ ID NO: 31 and SEQ ID NO: 32); (SEQ ID NO: 33 and SEQ ID NO: 34); (SEQ ID NO: 35 and SEQ ID NO: 36); (SEQ ID NO: 37 and SEQ ID NO: 38); (SEQ ID NO: 39 and SEQ ID NO: 40).

Table 1 gives the list of the double-stranded oligonucleotide sequences used in the present invention. The gene targeted in humans by each corresponding double-stranded oligonucleotide sequence is given in the first column of the table. For TSP1, TRPV3, TRPM8, 4 different couples of oligonucleotides are shown, and two for CD36, integrin B3, TRPV2, TRPV6.

TABLE 1

| Target of the oligonucleotide | With dTdT | Without dT dT |
|---|---|---|
| TSP1 Sequence | SEQ ID NO 1: CCUUGACAACAACGUGGUGdTdT | SEQ ID NO 21: CCUUGACAACAACGUGGUG |
| TSP1a, cross species | SEQ ID NO 2: CACCACGUUGUUGUCAAGGdTdT | SEQ ID NO 22: CACCACGUUGUUGUCAAGG |
| TSP1 Sequence | SEQ ID NO 3: UACCCGAGACGAUUGUAUGdTdT | SEQ ID NO 23: UACCCGAGACGAUUGUAUG |
| TSP1b | SEQ ID NO 4: CAUACAAUCGUCUCGGGUAdTdT | SEQ ID NO 24: CAUACAAUCGUCUCGGGUA |
| TRPV3 Sequence | SEQ ID NO 5: CAAGGAGAGCGAACGCAUCdTdT | SEQ ID NO 25: CAAGGAGAGCGAACGCAUC |

TABLE 1-continued

| Target of the oligonucleotide | With dTdT | Without dT dT |
|---|---|---|
| TRPV3a | SEQ ID NO 6:<br>GAUGCGUUCGCUCUCCUUGdTdT | SEQ ID NO 26:<br>GAUGCGUUCGCUCUCCUUG |
| TRPV3 Sequence | SEQ ID NO 7:<br>AUGUACAGCGUCAUGAUCCdTdT | SEQ ID NO 27:<br>AUGUACAGCGUCAUGAUCC |
| TRPV3b, cross species | SEQ ID NO 8:<br>GGAUCAUGACGCUGUACAUdTdT | SEQ ID NO 28:<br>GGAUCAUGACGCUGUACAU |
| TRPM8 Sequence | SEQ ID NO 9:<br>UCUCUGAGCGCACUAUUCAdTdT | SEQ ID NO 29:<br>UCUCUGAGCGCACUAUUCA |
| TRPM8a | SEQ ID NO 10:<br>UGAAUAGUGCGCUCAGAGAdTdT | SEQ ID NO 30:<br>UGAAUAGUGCGCUCAGAGA |
| TRPM8 Sequence | SEQ ID NO 11:<br>UAUUCCGUUCGGUCAUCUAdTdT | SEQ ID NO 31:<br>UAUUCCGUUCGGUCAUCUA |
| TRPM8b | SEQ ID NO 12:<br>UAGAUGACCGAACGGAAUAdTdT | SEQ ID NO 32:<br>UAGAUGACCGAACGGAAUA |
| CD36 | SEQ ID NO 13:<br>UACAGACAGUUUUGGAUCUdTdT | SEQ ID NO 33:<br>UACAGACAGUUUUGGAUCU |
|  | SEQ ID NO 14:<br>AGAUCCAAAACUGUCUGUAdTdT | SEQ ID NO 34:<br>AGAUCCAAAACUGUCUGUA |
| integrin B3 | SEQ ID NO 15:<br>GGAGAAUCUGCUGAAGGAUdTdT | SEQ ID NO 35:<br>GGAGAAUCUGCUGAAGGAU |
|  | SEQ ID NO 16:<br>AUCCUUCAGCAGAUUCUCCdTdT | SEQ ID NO 36:<br>AUCCUUCAGCAGAUUCUCC |
| TRPV2 | SEQ ID NO 17:<br>UAAGAGUCAACCUCAACUAdTdT | SEQ ID NO 37:<br>UAAGAGUCAACCUCAACUA |
|  | SEQ ID NO 18:<br>UAGUUGAGGUUGACUCUUAdTdT | SEQ ID NO 38:<br>UAGUUGAGGUUGACUCUUA |
| TRPV6 | SEQ ID NO 19:<br>GGAAGACAGGCAAGAUCUCdTdT | SEQ ID NO 39:<br>GGAAGACAGGCAAGAUCUC |
|  | SEQ ID NO 20:<br>GAGAUCUUGCCUGUCUUCCdTdT | SEQ ID NO 40:<br>GAGAUCUUGCCUGUCUUCC |

The oligonucleotide sequences numbered from 1 to 20 comprise at the 3' end of each of the two said oligonucleotide sequences two deoxythymidines extending beyond the hybrid. The oligonucleotide sequences numbered from 21 to 40 do not comprise any nucleotide extending beyond the hybrid; the first oligonucleotide sequence (antisense strand) and the second oligonucleotide sequence (sense strand) have the same length, in Table 1, according to an advantageous embodiment of the invention.

The TSP1 expression in humans can be inhibited using either one of the following four different double stranded oligonucleotides which target the TSP1 mRNA:
  the double-stranded oligonucleotide consisting in SEQ ID NO: 1 and SEQ ID NO:2, which targets the portion of the TSP1 mRNA denoted TSP1a in table 1
  or the double-stranded oligonucleotide consisting in SEQ ID NO: 21 and SEQ ID NO: 22, which targets the portion of the TSP1 mRNA denoted TSP1a in table 1- or the double-stranded oligonucleotide consisting in SEQ ID NO: 3 and SEQ ID NO: 4, which targets the portion of the TSP1 mRNA denoted TSP1b in table 1
  or the double-stranded oligonucleotide consisting in SEQ ID NO: 23 and SEQ ID NO: 24 which targets the portion of the TSP1 mRNA denoted TSP1b in table 1.

Since the sequence denoted TSP1a in table 1 is fully conserved between several mammals, notably between human and mouse, the double-stranded oligonucleotide consisting in SEQ ID NO: 1 and SEQ ID NO: 2, or the double-stranded oligonucleotide consisting in SEQ ID NO: 21 and SEQ ID NO: 22 can be used to inhibit TSP1 expression in humans but also in other mammals.

The TRPV3 expression in humans can be inhibited using either one of the following four different double stranded oligonucleotides which target the TRPV3 mRNA:
  the double-stranded oligonucleotide consisting in SEQ ID NO: 5 and SEQ ID NO: 6, which targets the portion of the TRPV3 mRNA denoted TRPV3a in table 1
  or the double-stranded oligonucleotide consisting in SEQ ID NO: 25 and SEQ ID NO: 26, which targets the portion of the TRPV3 mRNA denoted TRPV3a in table 1
  or the double-stranded oligonucleotide consisting in SEQ ID NO: 7 and SEQ ID NO: 8, which targets the portion of the TRPV3 mRNA denoted TRPV3b in table 1
  or the double-stranded oligonucleotide consisting in SEQ ID NO: 27 and SEQ ID NO: 28 which targets the portion of the TRPV3 mRNA denoted TRPV3b in table 1

Since the sequence denoted TRPV3b in table 1 is fully conserved between several mammals, notably between human and mouse, the double-stranded oligonucleotide consisting in SEQ ID NO: 7 and SEQ ID NO: 8, or the double-stranded oligonucleotide consisting in SEQ ID NO: 27 and SEQ ID NO: 28 can be used to inhibit TRPV3 expression in humans but also in other mammals.

A double-stranded oligonucleotide which does not recognize any mammalian mRNA known to this day is used as a control in some in vitro and in vivo experiments. This double-stranded oligonucleotide consists in the following couple of sequences:

```
                                          SEQ ID NO: 43
Strand 1:   5'-GAUAGCAAUGACGAAUGCGUAdTdT-3'

SEQ ID NO: 44
Strand 2:   5'-UACGCAUUCGUCAUUGCUAUCdTdT-3'
```

It is to be noted that other controls can be substituted, and in vivo injection of the vehicle (PBS) is also used as a control.

In an advantageous embodiment, the double-stranded oligonucleotide is chosen from the following couples consisting in (SEQ ID NO: 1 and SEQ ID NO: 2); (SEQ ID NO: 3 and SEQ ID NO: 4); (SEQ ID NO: 5 and SEQ ID NO: 6); (SEQ ID NO: 7 and SEQ ID NO: 8); (SEQ ID NO: 13 and SEQ ID NO: 14); (SEQ ID NO: 15 and SEQ ID NO: 16); (SEQ ID NO: 17 and SEQ ID NO: 18); (SEQ ID NO: 21 and SEQ ID NO: 22); (SEQ ID NO: 23 and SEQ ID NO: 24); (SEQ ID NO: 25 and SEQ ID NO: 26); (SEQ ID NO: 27 and SEQ ID NO: 28); (SEQ ID NO: 33 and SEQ ID NO: 34); (SEQ ID NO: 35 and SEQ ID NO: 36); (SEQ ID NO: 37 and SEQ ID NO: 38).

In a more advantageous embodiment, the double-stranded oligonucleotide is chosen from the following couples consisting in (SEQ ID NO: 1 and SEQ ID NO: 2); (SEQ ID NO: 3 and SEQ ID NO: 4); (SEQ ID NO: 5 and SEQ ID NO: 6); (SEQ ID NO: 7 and SEQ ID NO: 8); (SEQ ID NO: 17 and SEQ ID NO: 18); (SEQ ID NO: 21 and SEQ ID NO: 22); (SEQ ID NO: 23 and SEQ ID NO: 24); (SEQ ID NO: 25 and SEQ ID NO: 26); (SEQ ID NO: 27 and SEQ ID NO: 28); (SEQ ID NO: 37 and SEQ ID NO: 38).

To develop an oligonucleotide as a therapeutic drug inhibiting a given mRNA in humans, it is particularly advantageous that the double stranded oligonucleotide targets a sequence fully conserved between humans and mouse. This property allows of evaluation of the oligonucleotide efficiency and toxicity in preclinical models before its administration to humans. In a particular advantageous embodiment, the double-stranded oligonucleotide is chosen from the following couples consisting in (SEQ ID NO: 1 and SEQ ID NO: 2); (SEQ ID NO: 7 and SEQ ID NO: 8); (SEQ ID NO: 21 and SEQ ID NO: 22); (SEQ ID NO: 27 and SEQ ID NO: 28).

In another embodiment, the invention relates to the use of a product containing or consisting in:
  at least a double-stranded oligonucleotide above-defined,
  at least an anti-angiogenic agent,
for the manufacture of a combination product for a simultaneous, separate, or spread over time use for the prevention or the treatment of primary tumors or invasive or metastatic tumors.

In another embodiment, the invention relates to the use of a product containing or consisting in:
  at least a double-stranded oligonucleotide above-defined,
  at least an anti-tumoral agent,
for the manufacture of a combination product for a simultaneous, separate, or spread over time use for the prevention or the treatment of primary tumors or invasive or metastatic tumors.

In another embodiment, the invention relates to the use of a product containing or consisting in:
  at least a double-stranded oligonucleotide above-defined,
  at least an anti-angiogenic agent,
  at least an anti-tumoral agent,
for the manufacture of a combination product for a simultaneous, separate, or spread over time use for the prevention or the treatment of primary tumors or invasive or metastatic tumors.

In an advantageous embodiment, the drug is combined with an anti-tumoral therapy, such as radiotherapy or chemotherapy.

In an advantageous embodiment, the anti-angiogenic agent is chosen from the group comprising Cilengitide, Vandetanib, Lenalidomide, Thalidomide, Arsenic Trioxide, Bevacizumab, anti-VEGFR-1, anti-VEGFR-2, anti-PDGFR, anti-FMS-FLT-3, anti-TK1.

In an advantageous embodiment, the anti-tumoral agent is chosen from the group comprising alkylating agents, such as Bendamustine, Temozolomide, Mechlorethamine, Cyclophosphamide, Carmustine, Cisplatine, Busulfan, Thiotepa, or Decarbazine, anti-metabolite agents, such as Pentostatine, Methotrexate, Pemetrexed, Floxuridine, Fluorouracil, Cytaraine, Mercaptopurine or Thiguanine, cytotoxic antibiotics such as Rubitecan, Mitomycine C, Daunorubicin, Doxorubicine, Bleomycin, Plicamycin, Mitoxantrone HCl, or Oxaliplatine, plant derivatives, such as Vinorelbine, BMS 184476, Vincristine sulfate, Vinblastine, Docetaxel taxol.

In another advantageous embodiment, the primary tumor or invasive of metastatic tumor is a solid tumor or a lymphoproliferative tumor.

In a more advantageous embodiment, the solid tumor is a prostate tumor, a liver tumor, hepatic adenomas, focal nodular hyperplasia, a brain tumor such as glioma, a breast tumor, a kidney tumor, a lung tumor such as non-small cell lung carcinoma, small cell lung carcinoma, pleuropulmonary blastoma and carcinoid tumor, a bone tumor such as osteoma, osteochondroma, aneurysmal bone cyst, and fibrous dysplasia, osteosarcoma, chondrosarcoma, Ewing's sarcoma, malignant fibrous histiocytoma, fibrosarcoma, a stomach cancer, a colon tumor, a small bowel tumor, a esophageal tumor, a pancreatic tumor, a sarcoma, a cervical tumor, a gall blader tumor, a melanoma.

In another more advantageous embodiment, lymphoproliferative tumor is Leukemia, Lymphoma, or a Multiple myeloma.

In conformity with the present invention, the inhibitor of protein activity can be an antibody against TSP1 protein or one protein controlling the expression or mediating the activity of TSP1, such as TRPV2, TRPV3, TRPV6, TRPM8, CD36, B3 integrin, in instance.

In another aspect, the invention relates to a pharmaceutical composition.

In a general embodiment, the pharmaceutical composition comprises as active substance, at least
  one inhibitor of protein expression, which inhibits the expression of:
    TSP1 protein, or
    a protein, which controls the expression of TSP1 or mediates the activity of TSP1 or,
  one inhibitor of protein activity, said inhibitor inhibiting the activity of:
    the TSP1 protein, in particular the activity responsible for the stimulation of cell migration, or
    one protein which controls the expression or mediates the activity of TSP1, in association with a pharmaceutically acceptable vehicle.

In an advantageous embodiment, the inhibitor of protein expression inhibits the expression of proteins chosen from the group comprising TSP1, TRPV2, TRPV3, TRPV6, TRPM8, CD36, or B3 integrin.

In a more advantageous embodiment, the inhibitor of protein expression inhibits the expression of proteins chosen from the group comprising TSP1, TRPV2, TRPV3, CD36, or B3 integrin.

In a particular advantageous embodiment, inhibitor of protein expression inhibits the expression of proteins chosen from the group comprising TSP1, TRPV2, TRPV3.

In another advantageous embodiment, inhibitor of the protein expression is a double-stranded oligonucleotide or a single-stranded oligonucleotide.

In another embodiment, the inhibitor of the protein expression in the pharmaceutical composition of the present invention is:
  a double-stranded oligonucleotide comprising two oligonucleotide sequences, (a) and (b), forming a hybrid,
  wherein the oligonucleotide sequence (a)
    is either complementary to the oligonucleotide sequence (b),
    or presents less than 40% mismatches with said oligonucleotide sequence (b), and
  wherein the oligonucleotide sequence (a)
    is either complementary to a target sequence belonging to the RNA or DNA molecule coding one of the proteins above-defined, the expression of which is to be inhibited,
    or presents less than 40% mismatches with a target sequence belonging to the RNA or DNA molecule coding one of the proteins above-defined, the expression of which is to be inhibited,
  or a fragment of the above-defined double-stranded oligonucleotides (a) and (b), comprising two complementary fragments of the respective above-defined oligonucleotide sequences (a) and (b), provided that said fragment conserves the property of inhibiting the expression of one of the proteins above-defined.

The oligonucleotide sequence (a) is preferably complementary to the oligonucleotide sequence (b), but can comprise 1-8 mismatches, particularly 5, more particularly 3 mismatches, still more particularly 1 mismatch with the oligonucleotide sequence (b).

The oligonucleotide sequence (a) is preferably complementary to the target sequence, but can comprise 1-8 mismatches, particularly 5, more particularly 3 mismatches, still more particularly 1 mismatch with the target sequence; this application is particular when the length of the target sequence is 21 nucleotides.

In another embodiment, inhibitor of the protein expression in the pharmaceutical composition of the present invention is:
  a double-stranded oligonucleotide comprising two oligonucleotide sequences, (a) and (b), forming a hybrid, wherein each oligonucleotide sequence comprises at one of its 3' or 5' ends, one to five unpaired nucleotides forming single-stranded ends extending beyond the hybrid, wherein the part inside the hybrid of the oligonucleotide sequence (a)
    is either complementary to the oligonucleotide sequence (b),
    or presents less than 40% mismatches with said oligonucleotide sequence (b), and
  wherein the oligonucleotide sequence (a)
    is either complementary to a target sequence belonging to the RNA, or DNA molecule coding one of the proteins above-defined, the expression of which is to be inhibited,
    or presents less than 40% mismatches with a target sequence belonging to the RNA or DNA molecule coding one of the proteins above-defined, the expression of which is to be inhibited,
  or a fragment of the above-defined double-stranded oligonucleotides (a) and (b), comprising two complementary fragments of the respective above-defined oligonucleotide sequences (a) and (b), provided that said fragment conserves the property of inhibiting the expression of one of the proteins above-defined.

The oligonucleotide sequence (a) is preferably complementary to the oligonucleotide sequence (b), but can comprise 1-8 mismatches, particularly 5, more particularly 3 mismatches, still more particularly 1 mismatch with the oligonucleotide sequence (b).

The oligonucleotide sequence (a) is preferably complementary to the target sequence, but can comprise 1-8 mismatches, particularly 5, more particularly 3 mismatches, still more particularly 1 mismatch with the target sequence; this application is particular when the length of the target sequence is 21 nucleotides.

In the pharmaceutical compositions of the present invention, oligonucleotide sequence complementary to the target sequence comprises from 15 to 25 nucleotides.

In an advantageous embodiment, the double-stranded oligonucleotide comprises, at the 3' end of each of the two said oligonucleotide sequences 1 to 5 nucleotides, preferably 2 to 3 nucleotides, extending beyond the hybrid.

The nucleotides extending beyond the hybrid can be complementary or not to the target sequence.

The nucleotides extending beyond the hybrid can be any natural nucleotide.

In a more advantageous embodiment, the nucleotides extending beyond the hybrid are deoxythymidines.

In a particular embodiment, the expression of the target sequence represented by SEQ ID NO: 41 (TSP1) is inhibited by the double-stranded oligonucleotide described in the present invention.

In another particular embodiment, the expression of the target sequence represented by SEQ ID NO: 43 (TRPV3) is inhibited by the double-stranded oligonucleotide described in the present invention.

In another particular embodiment, the pharmaceutical composition of the present invention comprises as active substance, the double-stranded oligonucleotide chosen from the following couples consisting in (SEQ ID NO: 1 and SEQ ID NO: 2); (SEQ ID NO: 3 and SEQ ID NO: 4); (SEQ ID NO: 5 and SEQ ID NO: 6); (SEQ ID NO: 7 and SEQ ID NO: 8); (SEQ ID NO: 9 and SEQ ID NO: 10); (SEQ ID NO: 11 and SEQ ID NO: 12); (SEQ ID NO: 13 and SEQ ID NO: 14); (SEQ ID NO: 15 and SEQ ID NO: 16); (SEQ ID NO: 17 and SEQ ID NO: 18); (SEQ ID NO: 19 and SEQ ID NO: 20); (SEQ ID NO: 21 and SEQ ID NO: 22); (SEQ ID NO: 23 and SEQ ID NO: 24); (SEQ ID NO: 25 and SEQ ID NO: 26); (SEQ ID NO: 27 and SEQ ID NO: 28); (SEQ ID NO: 29 and SEQ ID NO: 30); (SEQ ID NO: 31 and SEQ ID NO: 32); (SEQ ID NO: 33 and SEQ ID NO: 34); (SEQ ID NO: 35 and SEQ ID NO: 36); (SEQ ID NO: 37 and SEQ ID NO: 38); (SEQ ID NO: 39 and SEQ ID NO: 40).

In an advantageous embodiment, the pharmaceutical composition of the present invention comprises as active substance, the double-stranded oligonucleotide chosen from the following couples consisting in (SEQ ID NO: 1 and SEQ ID NO: 2); (SEQ ID NO: 3 and SEQ ID NO: 4); (SEQ ID NO: 5 and SEQ ID NO: 6); (SEQ ID NO: 7 and SEQ ID NO: 8); (SEQ ID NO: 13 and SEQ ID NO: 14); (SEQ ID NO: 15 and SEQ ID NO: 16); (SEQ ID NO: 17 and SEQ ID NO: 18); (SEQ ID NO: 21 and SEQ ID NO: 22); (SEQ ID NO: 23 and SEQ ID NO: 24); (SEQ ID NO: 25 and SEQ ID NO: 26); (SEQ ID NO: 27 and SEQ ID NO: 28); (SEQ ID NO: 33 and SEQ ID NO: 34); (SEQ ID NO: 35 and SEQ ID NO: 36); (SEQ ID NO: 37 and SEQ ID NO: 38).

In a more advantageous embodiment, the pharmaceutical composition of the present invention comprises as active substance, the double-stranded oligonucleotide chosen from the following couples consisting in (SEQ ID NO: 1 and SEQ ID NO: 2); (SEQ ID NO: 3 and SEQ ID NO: 4); (SEQ ID NO: 5 and SEQ ID NO: 6); (SEQ ID NO: 7 and SEQ ID NO: 8); (SEQ ID NO: 17 and SEQ ID NO: 18); (SEQ ID NO: 21 and SEQ ID NO: 22); (SEQ ID NO: 23 and SEQ ID NO: 24); (SEQ ID NO: 25 and SEQ ID NO: 26); (SEQ ID NO: 27 and SEQ ID NO: 28); (SEQ ID NO: 37 and SEQ ID NO: 38).

In a particular advantageous embodiment, the pharmaceutical composition of the present invention comprises as active substance, the double-stranded oligonucleotide chosen from the following couples consisting in (SEQ ID NO: 1 and SEQ ID NO: 2); (SEQ ID NO: 7 and SEQ ID NO: 8); (SEQ ID NO: 21 and SEQ ID NO: 22); (SEQ ID NO: 27 and SEQ ID NO: 28).

In an advantageous embodiment, the pharmaceutically acceptable vehicle is a saline solution.

In another advantageous embodiment, the double-stranded oligonucleotide used in the pharmaceutical composition of the present invention is coupled with cholesterol or substances enabling penetration of said double-stranded oligonucleotide into the cells.

In another more advantageous embodiment, the substances enabling penetration of said double-stranded oligonucleotide into the cells are for instance liposomes, lipid-based agents, nanoparticles, magnetic spheres, polyethyleneimine derivatives.

In an advantageous embodiment, the active substance is formulated for the administration at a dose in the range of 0, 05 to 50 mg/kg, in particular 0, 1 to 20 mg/kg.

The active substance comprising the double-stranded oligonucleotide can be administrated at a modified but sufficient dose according to the application way or the form of the active substance.

In an advantageous embodiment, the active substance is formulated for one of the following administrations: intravenous, intraperitoneal, subcutaneous, intramuscular, nasal instillation, sublingual, intra rectal, direct injection in the tumor, topical or oral.

The oligonucleotides of the present invention can be either transfected in cells which are then injected in the tissues, or be directly injected in the tissues by, for example local, systemic, aerosol route.

In an advantageous embodiment, the pharmaceutical composition comprises, as active substance, a product containing or consisting in:
at least a double-stranded oligonucleotide above-defined
at least an anti-angiogenic agent,
as combination product for a simultaneous, separate, or spread over time use.

In a preferred embodiment, the pharmaceutical composition comprises, as active substance, a product containing or consisting in:
at least a double-stranded oligonucleotide above-defined,
at least an anti-tumoral agent,
as combination product for a simultaneous, separate, or spread over time use.

In a preferred embodiment, the pharmaceutical composition comprises, as active substance, a product containing or consisting in:
at least a double-stranded oligonucleotide above-defined,
at least an anti-angiogenic agent,
at least an anti-tumoral agent,
as combination product for a simultaneous, separate, or spread over time use.

The anti-angiogenic agent of the pharmaceutical composition of the invention can be chosen from the group comprising Cilengitide, Vandetanib, Lenalidomide, Thalidomide, Arsenic Trioxide, Bevacizumab, anti-VEGFR-1, anti-VEGFR-2, anti-PDGFR, anti-FMS-FLT-3, anti-TK1.

The anti-tumoral agent of the pharmaceutical composition of the invention can be chosen from the group comprising alkylating agents, such as Bendamustine, Temozolomide, Mechlorethamine, Cyclophosphamide, Carmustine, Cisplatine, Busulfan, Thiotepa, or Decarbazine, anti-metabolite agents, such as Pentostatine, Methotrexate, Pemetrexed, Floxuridine, Fluorouracil, Cytaraine, Mercaptopurine or Thiguanine, cytotoxic antibiotics such as Rubitecan, Mitomycine C, Daunorubicin, Doxorubicine, Bleomycin, Plicamycin, Mitoxantrone HCl, or Oxaliplatine, plant derivatives, such as Vinorelbine, BMS 184476, Vincristine sulfate, Vinblastine, Docetaxel taxol.

In another embodiment, the invention relates to the oligonucleotide sequence chosen from the following sequences: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40

All these sequences are new per se.

In another embodiment, the invention relates to the double-stranded oligonucleotides chosen from the following couples consisting in (SEQ ID NO: 1 and SEQ ID NO: 2); (SEQ ID NO: 3 and SEQ ID NO: 4); (SEQ ID NO: 5 and SEQ ID NO: 6); (SEQ ID NO: 7 and SEQ ID NO: 8); (SEQ ID NO: 9 and SEQ ID NO: 10); (SEQ ID NO: 11 and SEQ ID NO: 12); (SEQ ID NO: 13 and SEQ ID NO: 14); (SEQ ID NO: 15 and SEQ ID NO: 16); (SEQ ID NO: 17 and SEQ ID NO: 18); (SEQ ID NO: 19 and SEQ ID NO: 20); (SEQ ID NO: 21 and SEQ ID NO: 22); (SEQ ID NO: 23 and SEQ ID NO: 24); (SEQ ID NO: 25 and SEQ ID NO: 26); (SEQ ID NO: 27 and SEQ ID NO: 28); (SEQ ID NO: 29 and SEQ ID NO: 30); (SEQ ID NO: 31 and SEQ ID NO: 32); (SEQ ID NO: 33 and SEQ ID NO: 34); (SEQ ID NO: 35 and SEQ ID NO: 36); (SEQ ID NO: 37 and SEQ ID NO: 38); (SEQ ID NO: 39 and SEQ ID NO: 40).

In an advantageous embodiment, the invention relates to the double-stranded oligonucleotides chosen from the following couples consisting in (SEQ ID NO: 1 and SEQ ID NO: 2); (SEQ ID NO: 3 and SEQ ID NO: 4); (SEQ ID NO: 5 and SEQ ID NO: 6); (SEQ ID NO: 7 and SEQ ID NO: 8); (SEQ ID NO: 13 and SEQ ID NO: 14); (SEQ ID NO: 15 and SEQ ID NO: 16); (SEQ ID NO: 17 and SEQ ID NO: 18); (SEQ ID NO: 21 and SEQ ID NO: 22); (SEQ ID NO: 23 and SEQ ID NO: 24); (SEQ ID NO: 25 and SEQ ID NO: 26); (SEQ ID NO: 27 and SEQ ID NO: 28); (SEQ ID NO: 33 and SEQ ID NO: 34); (SEQ ID NO: 35 and SEQ ID NO: 36); (SEQ ID NO: 37 and SEQ ID NO: 38).

In an advantageous embodiment, the invention relates to the double-stranded oligonucleotides chosen from the following couples consisting in (SEQ ID NO: 1 and SEQ ID NO: 2); (SEQ ID NO: 3 and SEQ ID NO: 4); (SEQ ID NO: 5 and SEQ ID NO: 6); (SEQ ID NO: 7 and SEQ ID NO: 8); (SEQ ID NO: 17 and SEQ ID NO: 18); (SEQ ID NO: 21 and SEQ ID NO: 22); (SEQ ID NO: 23 and SEQ ID NO: 24); (SEQ ID NO: 25 and SEQ ID NO: 26); (SEQ ID NO: 27 and SEQ ID NO: 28); (SEQ ID NO: 37 and SEQ ID NO: 38).

In a particular advantageous embodiment, the invention relates to the double-stranded oligonucleotide chosen from the following couples consisting in (SEQ ID NO: 1 and SEQ ID NO: 2); (SEQ ID NO: 7 and SEQ ID NO: 8); (SEQ ID NO: 21 and SEQ ID NO: 22); (SEQ ID NO: 27 and SEQ ID NO: 28).

All these double-stranded oligonucleotides are new per se.

The present invention is illustrated by the following Figures and examples, which are in no way the limitation of the scope of the invention.

DESCRIPTION OF THE FIGURES

FIG. 2A represents TSP1 expression in C4-2 cells treated for 2 h by vehicle (left) or thapsigargin (1 µM) (right). TSP1 expression is visualized by indirect immunofluorescence.

FIG. 2B represents TSP1 secretion in the cell culture medium by C4-2 cells treated for 2 h by vehicle (left) or thapsigargin (1 µM) (right). The secreted TSP1 is measured by western blotting in the cell culture medium.

FIG. 2C represents TSP1 expression in C4-2 cells treated for 2 h with camphor at the indicated doses. TSP1 expression is visualized by indirect immuno fluorescence.

FIG. 2D represents TSP1 secretion in the cell culture medium by C4-2 cells treated for 2 h by vehicle or camphor at the indicated doses. The secreted TSP1 is measured by western blotting in the cell culture medium.

FIG. 2E represents TSP1 mRNA level in C4-2 cells after 6 h of treatment by camphor at the indicated doses (mean±SEM, n=3). mRNA level is normalized to cyclophilin A.

FIG. 2F shows TRPV3 (black bars) and TRPM8 (grey bars) mRNA levels measured in the indicated prostate tumor cell lines. Results (mean±SEM, n>3) are normalized to cyclophilin A mRNA level and expressed in arbitrary units.

FIG. 2G represents the detection by western-blot of TRPV3 protein in indicated prostate cell lines. Tubulin was used as a loading control.

FIG. 2H represents TSP1 and TRPV3 expression in C4-2 cells 48 h after transfection of TRPV3a siRNA.

FIG. 2I represents TSP1 mRNA level of C4-2 cells transfected by the indicated siRNAs. Results, normalized to cyclophilin A mRNA level are measured 2 day after transfection (mean±SEM, n>3).

FIG. 2J represents the migration capacity towards fresh culture medium of C4-2 cells transfected with the indicated siRNAs. Cells were seeded in the upper chamber 2 days after transfection and the number of cells that had migrated was counted 18 h later. Result are expressed as the percentage of migrating cells as compared to cells migrating in the control condition (mean±SEM, n=3). The experiment was repeated 3 times with comparable results.

EXAMPLES

Figure 1A:
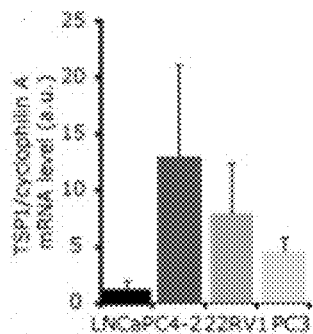
FIG. 1A represents TSP1 mRNA level in androgen-dependent (LNCaP), castration-resistant (C4-2 and 22RV1), or androgen-independent (PC3) prostate tumor cells. Results (mean±SEM, n>3) are normalized to the cyclophilin A mRNA level and expressed in arbitrary units (LNCaP set to 1).

The following examples have been carried out according to the experimental procedures hereafter described.

Reagents and siRNAs

Camphor and thapsigargin were purchased from Sigma-Aldrich (Saint-Quentin Fallavier, France). TSP1 antibodies (Ab1, Ab-4 and Ab-11) were from Neomarkers (Thermo scientific, Fremont, Calif., USA), TRPV3 antibodies from TEBU (Le Perray en Yvelines, France) and Tubulin from Sigma-Aldrich (Saint-Quentin Fallavier, France). Alexa-Fluor goat anti-rabbit 488 and Alexa-Fluor goat anti-mouse 568 were purchased from Molecular probes. SiRNAs were purchased from Sigma-Aldrich (Saint-Quentin Fallavier, France). The sequences used are indicated in the supplementary table 1.

Cell Lines

Cell line LNCaP is a human androgen-dependent prostate cell line. It expresses the androgen receptor and depends of androgen for its growth.

Cell line C4-2 and 22RV1 are human castration-resistant prostate tumor cell lines. They express the androgen receptor but no more depend on androgens for their growth.

Cell line PC3 is a human androgen-independent prostate cell line. PC3 cells no longer express the androgen receptor.

Cell Culture and Transfection

LNCaP and C4-2 cells were grown in RMPI containing 10% fetal calf serum, PC-3 cells in DMEM containing 10% fetal calf serum. The Hiperfect reagent (Qiagen, Courtaboeuf, France) was used to transfect cells in 24 wells plates with the indicated siRNAs (10 nM) as recommended by the manufacturer. A metabolic activity assay (WST1, Roche Diagnostics, Meylan France) was used to measure cell proliferation. To mimic hypoxia, cells were grown in the presence of 300 µM cobalt chloride for 48 h. For hypoxic conditions, cells were cultured at 37° C. with 5% CO2, 94% N2 and 1% O2 in a hypoxic incubator (Binder GmbH, Tuttligen, France).

Migration Assay

The migration capacity was measured using a modified Boyden Chamber. Cells (40,000) were seeded in RPMI 1% FBS in the upper part of a cell culture-chamber-insert system separated from the lower chamber by a 8 µm PET membrane (BD Biosciences, Le Pont de Claix, France). RPMI 10% FBS, or conditioned medium was added in the lower compartment. Eighteen hours later, non migrating cells in the upper compartment were scrapped off using a cotton swab. Cells on the lower side of the membrane were fixed with methanol at −20° C. and stained with Hoechst 33258 (Sigma-Aldrich, Saint-Quentin Fallavier, France). Membranes were then excised, mounted on a glass side with Glycergel (DAKO) and cells counted.

Real-Time RT-PCR siRNA and mRNA Analysis

Total RNA was isolated using TRIzol reagent (Invitrogen, Cergy Pontoise, France). RNA were retrotranscribed using a High capacity cDNA Reverse Transcription Kit (Applied Biosystems, Courtaboeuf, France). cDNA was quantified by real time PCR using the Power SYBR® Green PCR Master Mix (Applied Biosystems, Courtaboeuf, France). Human Cyclophilin A was used as an internal control. The sequences of the PCR primers are indicated in the supplementary table 2.

ELISA

TSP1 and VEGF protein contents in cell homogenates and supernatant were measured by ELISA (quantikine, R&D, Lille, France).

Calcium Imaging

Fluorescence imaging was carried out in Hank's balanced salt solution (HBSS) containing 142 mM NaCl, 5.6 mM KCl, 1 mM $MgCl_2$, 2 mM $CaCl_2$, 0.34 mM $Na_2HPO_4$, 0.44 mM $KH_2PO_4$, 10 mM HEPES, and 5.6 mM glucose. Cytosolic calcium concentration was measured using Fura-2 loaded cells (2 µM) as previously described (Mariot et al., 2002). The intracellular calcium concentration was derived from the ratio of the fluorescence intensities for each of the excitation wavelengths (F340/F380) and from the Grynkiewicz equation (Grynkiewicz et al., 1985).

Animals, siRNA Injection and Tumorigenicity Assays

Studies involving animals, including housing and care, method of euthanasia and experimental protocols were conducted in accordance with the local animal ethical committee in the Institut André Lwoff in Villejuif, France. Tumor cells ($2\times10^6$ cells/mouse) were injected subcutaneously in 50% (v:v) matrigel (BD biosciences, Le Pont de Claix, France) to 6-8 weeks old male nude mice and measured every day. When tumors grew exponentially, siRNA diluted in PBS were injected i.p. on a daily basis (120 µg/kg). Tumor volume was estimated using the formula: length×width$^2$×0.5.

Subjects

Prostate tissue samples were obtained from 14 patients who underwent radical prostatectomy at the Centre Hospitalier Lyon Sud (Lyon, France) and 12 from the Cochin Hospital (Paris, France). Written consent was obtained from each patient. Immediately after prostate removal small pieces of tissues were gross dissected by the pathologist, snap-frozen and stored in liquid nitrogen until analysis in tumor banks of the Centre hospitalier Lyon Sud and of the groupe hospitalier Cochin-Saint Vincent de Paul. Histological analysis of a frozen section was performed for each sample by the same pathologist before RNA extraction. The fragments fully constituted of cancerous glands were selected and named "tumor" samples, whereas those that did not contain cancerous tissue were selected and named "peritumoral tissue".

Example 1

TSP1 Expression is Increased in Hormone-Refractory Cancer Prostate Cells

Figure 1B:
FIG. 1B represents corresponding TSP1 protein level in androgen-dependent (LNCaP), castration-resistant (C4-2 and 22RV1), or androgen-independent (PC3) prostate tumor cells. Tubulin was used as a loading control.
Figure 1C:
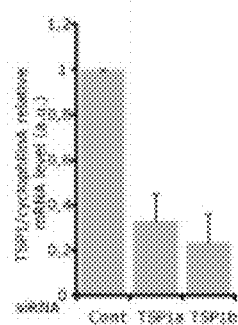
FIG. 1C represents TSP1 mRNA level in C4-2 cells 48 h after transfection with two different siRNAs targeting the TSP1 mRNA. Results, normalized to the cyclophilin A mRNA level in the same cells, are expressed as arbitrary unit, mean±SEM of 3 independent experiments.
Figure 1D:
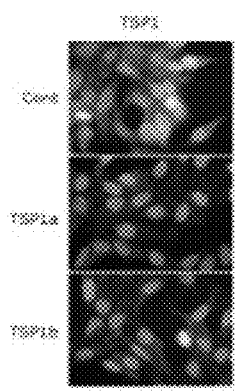
FIG. 1D represents the TSP1 expression, visualized by indirect immunofluorescence in C4-2 cells 48 h after transfection with TSP1a- or TSP1b-siRNA.
Figure 1E:
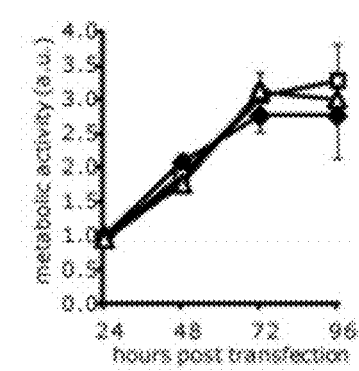
FIG. 1E represents the metabolic activity of C4-2 cells after transfection of TSP1a- or TSP1b-siRNA.
Figure 1F:
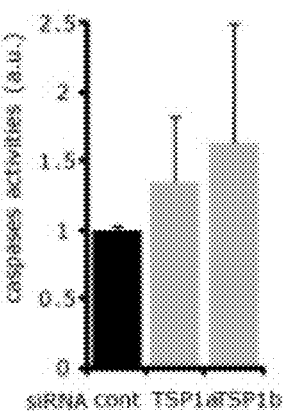
FIG. 1F represents the enzymatic activity of caspases 3 and 7 measured 48 h after transfection of C4-2 cells with the TSP1a- or TSP1b-siRNA. Results are not statistically different between control or TSP1-siRNA transfected cells.

The TSP1 promoter is methylated in the androgen-dependent prostate cell line LNCaP (Li et al., 1999) and accordingly, TSP1 mRNA and protein levels are very low in these cells (FIG. 1A and FIG. 1B). Interestingly, a sustained TSP1 expression was found in C4-2 cells, which were established from LNCaP tumors recurring in mice after castration (Thalmann et al., 1994). TSP1 was also found expressed, at the mRNA (FIG. 1A) and protein (FIG. 1B) levels, in the castration-resistant prostate tumor cell line R22RV1 (Sramkoski et al., 1999), and in the androgen-independent cell line PC3. To study the function of TSP1 in prostate carcinoma cells, a first siRNA was designed to target a sequence fully conserved between the mouse and the human sequences (TSP1a-siRNA) and a second one was designed to target specifically the human mRNA (TSP1b-siRNA). In C4-2 cells, the two siRNAs silenced TSP1 expression over 70% at the mRNA (FIG. 1C) and protein level (FIG. 1D), with no effect on cell proliferation (FIG. 1E) or apoptosis (FIG. 1F).

Example 2

TSP1 Stimulates the Migration of Prostate Tumor Cells

Figure 1G:
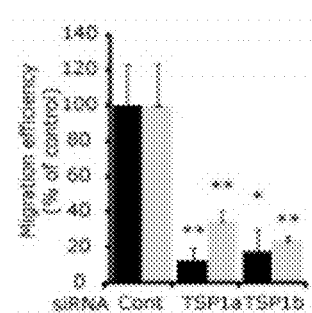
FIG. 1G represents the migration capacity towards fresh culture medium of C4-2 (black bars) or PC3 cells (grey bars) transfected with the indicated siRNAs. Two days after transfection, cells were seeded in the upper part of the Boyden chamber and the number of cells that had migrated towards fresh medium was counted 18 h later. Result are expressed as the percentage of migrating cells as compared to cells migrating in the control condition (mean±SEM, n=3). The experiment was repeated 3 times with comparable results.
Figure 1H:
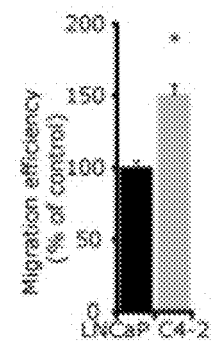
FIG. 1H represents the migration capacity of LNCaP towards conditioned medium from LNCaP or C4-2 cells. LNCaP (black bars) or C4-2 cells (grey bars) were plated in the lower part of Boyden chambers. 2 days later, LNCaP cells were seeded in the upper chamber and the number of migrating cells counted 18 h later. Results are expressed as in G.
Figure 1I:
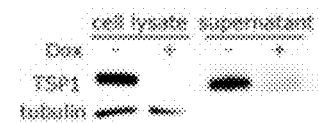
FIG. 1I represents TSP1 expression, measured by western blotting, in cellular homogenates and in the conditioned medium of JT8 cells cultured for 2 days in the presence (dox+) or absence (dox−) of doxycycline. JT8 cells are fibrosarcoma cells stably transfected with a tet-repressible plasmid coding for TSP1.
Figure 1J:
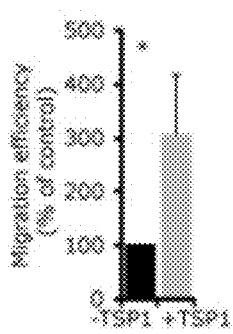
FIG. 1J represents the migration of C4-2 cells towards the medium conditioned by TSP1-inducible JT8 cells grown in the presence of doxycycline to repress TSP1 expression or in absence of doxycycline to induce TSP1. Results are expressed as in G.

Boyden chambers were used to study a potential role of TSP1 on the migration of prostate tumor cells. TSP1 silencing strongly inhibited the migration of C4-2 cells (FIG. 1G). This effect was not dependent upon the expression of the androgen receptor because the migration of PC3 cells was also strongly affected by TSP1 silencing (FIG. 1G). Conversely, the migration of LNCaP cells, which do not express TSP1, was stimulated when cells migrated towards C4-2 cells-conditioned medium (FIG. 1H). To further establish the role of TSP1 on the migration of prostate tumor cells, a cell line, JT8, where the production of TSP1 is under the control of a tetracycline-repressible promoter was used (Filleur et al., 2001). Conditioned medium of JT8 cells was prepared in the presence of doxycycline to repress TSP1 expression, or in its absence to induce TSP1 expression (FIG. 1I). The migration of C4-2 cells towards these two media was then measured. The presence of TSP1 strongly increased the capacity of cells to migrate (FIG. 1J).

Figure 1K:
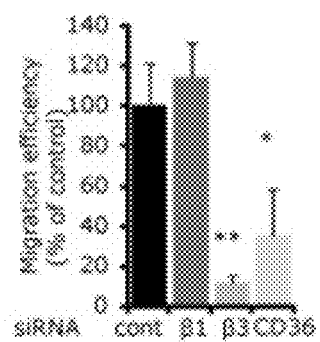
FIG. 1K represents the migration capacity of C4-2 cells transfected with the indicated siRNAs. Two days after transfection, cells were plated in the upper part of the Boyden chamber and the number of cells that had migrated towards fresh medium was counted 2 days later. Results are expressed as in FIG. 1C.
Figure 1L:
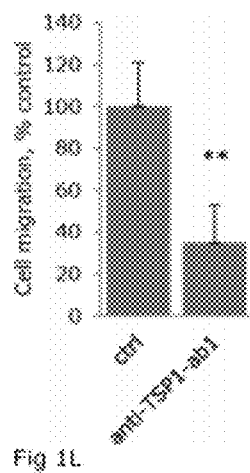
FIG. 1L represents the migration capacity of C4-2 towards C4-2-conditioned medium in the absence or presence of an antibody which inhibits the binding of TSP1 to CD36. C4-2 cells were plated in the lower part of Boyden chambers. 2 days later, C4-2 cells were plated in the upper chamber in control medium or in medium containing 1 µg/ml of, TSP1-antibody Ab1 (Clone A4.1 from neomarkers, Thermo scientific, Fremont, Calif., USA). When the TSP1-Ab1 antibody was added in the upper chamber, it was also added at the same concentration in the lower chamber. After a 18 h incubation, migrating cells were counted.

The activity of TSP1 is mediated by several kinds of receptors, in particular integrins comprising the subunits β1 or β3, and the CD36 receptor. Binding of TSP1 to CD36 has been shown to mediate the antiangiogenic effects of TSP1. In the present invention, specific siRNAs were designed to target respectively CD36, β1 and β3 integrins. Silencing β1 had no effect on the migration properties of C4-2 cells (FIG. 1K). In contrast, silencing CD36 or β3 strongly reduced the C4-2 migration in the Boyden assay (FIG. 1K). In addition, TSP1 antibodies that inhibit its binding to the CD36 receptor (TSP1 Ab1, clone A4.1) impaired the migration of C4-2 cells (FIG. 1L), demonstrating that the binding of TSP1 to CD36 mediates the antiangiogenic effects of TSP1 and its capacity to induce migration. The above mentioned results show that TSP1 is expressed at much higher levels (mRNA and protein) in C4-2, 22RV1 and PC3 cells than in LNCaP cells. Transfection of C4-2 cells by 10 nM of TSP1a-siRNA or TSP1b-siRNA significantly reduces the TSP1 mRNA level (FIG. 1C) and protein level (FIG. 1D), without affecting cell proliferation (FIG. 1E).

Example 3

TSP1 Expression and Secretion are Regulated by Calcium in Prostate Tumor Cells

TSP1 contains a calcium-binding domain and calcium affects TSP1 folding (Adams, 2004). The question is whether an increase in the cytosolic calcium concentration in prostate tumor cells could regulate TSP1 expression and/or secretion. For this purpose, C4-2 cells were treated with thapsigargin, an inhibitor of SERCA pump, which increases the intracellular calcium concentration ($Ca^{++}_i$). A 2 h treatment with thapsigargin resulted into a rapid depletion of TSP1 from the cytosol (FIG. 2A) and secretion into the culture medium (FIG. 2B). The calcium channels TRPV2 (Monet et al., 2010), TRPV6 (Fixemer et al., 2003), TRPM8 (FIG. 2J), and TRPV3 (FIGS. 2F and 2G) are expressed in prostate tumor cells. Camphor is a well-established agonist of TRPV3 channel (Moqrich et al., 2005; Vogt-Eisele et al., 2007) similarly stimulated TSP1 secretion (FIGS. 2C and 2D). In addition, a 6 h treatment by camphor induced a dose dependent increase in TSP1 mRNA level (FIG. 2E). These results establish that calcium regulates both TSP1 mRNA level and secretion in prostate tumor cells.

Example 4

Expression of TRP Channels and Regulation of TSP1 in Prostate Tumor Cells

The expression of two TRP channels, TRPM8 and TRPV3, was analysed in prostate cell lines. TRPM8 was expressed in LNCaP and C4-2 cells but undetectable in 22RV1 and at a very low level only in PC3 cells (FIG. 2F). In contrast, TRPV3 was expressed in all these 4 prostate cell lines (FIG. 2F), including the androgen-independent PC3 cells. The TRPV3 mRNA was upregulated in the castration-resistant cell line C4-2 as compared to its parental androgen-dependent cell line LNCaP. However, the results of invention clearly show that, at the protein level, TRPV3 is strongly expressed in LNCaP cells (FIG. 2G). Then it was analysed whether the expression of TRP channels could regulate TSP1 expression. Silencing TRPV3 reduced TSP1 protein expression (FIG. 2H). At least 4 channels of the TRP family, TRPV2, TRPV3, TRPV6 and TRPM8, stimulate TSP1, as their silencing resulted into a reduced TSP1 mRNA level (FIG. 2I). In contrast, TRPC4 and TRPC6 repressed TSP1, and their silencing increased its mRNA level in C4-2 cells (FIG. 2I, 2J). TRPC1, TRPC3 or ORAI had no significant effect on TSP1 expression (FIG. 2I).

Example 5

TRPV3 Channel is Involved in the Control of Prostate Cancer Cell Migration

Figure 3A:
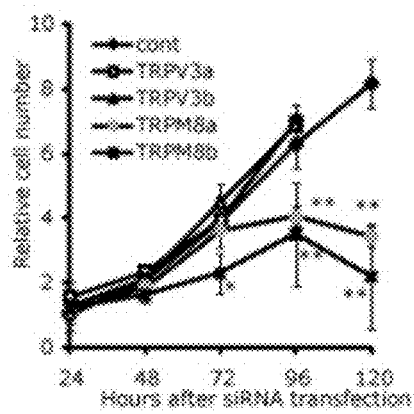
FIG. 3A represents the effects of TRPM8 and TRPV3 silencing on C4-2 cell proliferation. C4-2 cells were transfected with the indicated siRNAs. Their proliferation is measured by a metabolic assay (mean±SEM, n=3, representative of 3 separate experiments).
Figure 3B:
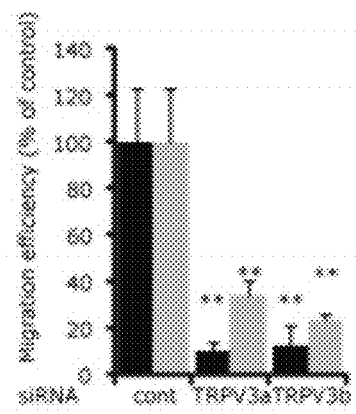
FIG. 3B represents the effects of TRPV3 silencing on the migration of C4-2 (black bars) or PC3 cells (grey bars). Cells were transfected by control, or 2 different TRPV3 siRNA as indicated, and a migration assay performed as in FIG. 1G.
Figure 3C:
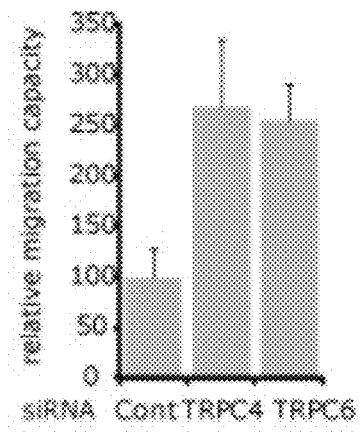
FIG. 3C represents the migration capacity of C4-2 cells transfected 2 days before with a cont- or TRPC4- or TRPC6-siRNA.

To address the possible role of TRP calcium channels on migration, focus was made on TRPV3 as this channel is well expressed in prostate carcinomas cells, whatever their dependence on androgens, and because, as opposed to TRPM8, TRPV3 silencing does not affect cell proliferation (FIG. 3A), a phenotype which could bias the interpretation of migration assays. TRPV3 silencing triggered a massive inhibition of cell migration in C4-2 and PC3 cells (FIG. 3B). In contrast, siRNAs targeting TRPC4 or TRPC6 stimulated C4-2 cells migration (FIG. 3C). All together, these results strongly suggest that the effects of TRP channels on migration could be mediated by TSP1.

Example 6

The Effects of TRPV3 on Cell Migration are Mediated by TSP1

Figure 3D:
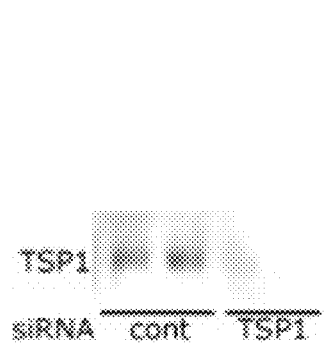
FIG. 3D represents Western blot detection of TSP1 in the culture medium of C4-2 cells transfected with cont- or TSP1-siRNA 48 h after transfection.
Figure 3E:
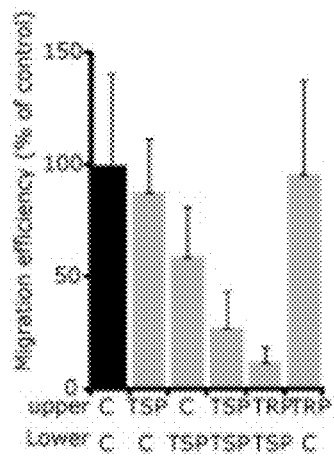
FIG. 3E represents the effects of TSP1 on migration capacity of C4-2 cells. C4-2 cells plated in the lower part of a Boyden chamber were transfected by either control-(noted C), or TSP1-siRNA (TSP). On the same day, a separate batch of cells was transfected by either control-, TSP1-, or TRPV3-siRNA (TRP). Three days later, these latter cells were trypsinized and seeded into the upper part of the Boyden chamber as indicated. Migration was quantified 18 h later and results expressed as a percentage of cells migrating in the control condition (cells transfected with a control-siRNA in the upper and lower part) (mean±SEM, n=3).

To further study the respective roles of TSP1 and TRPV3 in cell migration, C4-2 cells plated in the lower part of Boyden chambers were transfected by either control- or TSP1-siRNAs. Three days later, the TSP1 concentration was markedly reduced in the conditioned medium of TSP1-siRNA transfected cells (FIG. 3D). We then added in the upper part of the chambers C4-2 cells transfected 3 days earlier with control-, TSP1-, or TRPV3-siRNAs. As compared to control conditions (cells transfected by control siRNAs in the upper and lower chambers), silencing TSP1 simultaneously in the two compartments reduced migration by 70% (FIG. 3E). Interestingly, when TSP1 was silenced in a single compartment, either upper or lower, the migration capacity was only partially reduced, demonstrating that the migration effect is mediated by the secreted protein (FIG. 3E).

Silencing TRPV3 in the upper compartment drastically repressed the migration of C4-2 cells migrating towards a medium depleted in TSP1. But importantly, this inhibition was completely abolished when TSP1 was present in the lower part of the Boyden chambers (FIG. 3E). This result demonstrates that the stimulation by TRPV3 of cell migration is mediated by the secreted TSP1.

Example 7

Figure 4A:
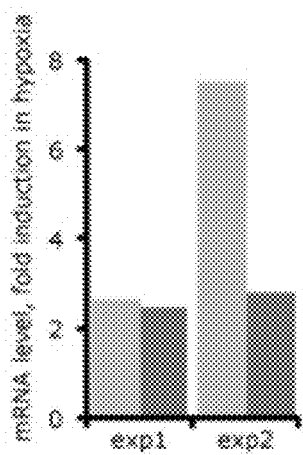
FIG. 4A represents TRPV3 (light grey bars) and TSP1 mRNA levels (dark grey bars) measured in C4-2 cells incubated in normoxia or in the presence of cobalt chloride 300 µM to mimic hypoxia. mRNA levels are quantified and normalized to cyclophilin A. Results are expressed as the ratio of mRNA levels in hypoxia to that in normoxia set to 1. The results from 2 independent experiments are shown.

Hypoxia Induces the Expression of TRPV3 and TSP1 and Increases the $[Ca^{++}]_i$ Resistance to hypoxic conditions is a common feature of advanced tumors. The TSP1 and TRPV3 mRNA levels, and the intracellular calcium concentration, were analysed in C4-2 cells under hypoxic conditions. A 48 h-treatment by 300 µM cobalt chloride, which induces the stabilization of Hif1a and Hif2a proteins (Yuan et al., 2003) and mimics the effects of hypoxia, strongly induced the TRPV3 and TSP1 mRNA levels (FIG. 4A).

Figure 4B:
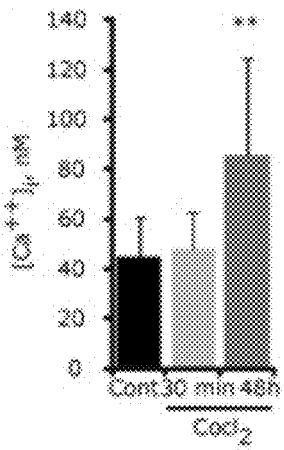
FIG. 4B represents intracellular calcium concentration in C4-2 cells grown in control conditions (cont) or in the presence of 300 µM $CoCl_2$ for 30 minutes or 48 hours (mean±SEM, n>120 cells per condition).

The intracellular calcium concentration was measured in C4-2 cells grown in control conditions or in the presence of cobalt chloride. The resting level, which was not modified after 30 min, was increased over two fold in cells incubated for 48 h in the presence of cobalt chloride (FIG. 4B).

Figure 4C:
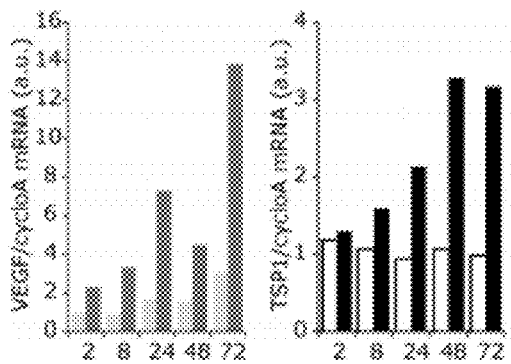
FIG. 4C represents VEGF and TSP1 mRNA levels in C4-2 cells incubated in 20% (normoxia) or 1% oxygen (hypoxia) for up to 72 h. Light grey bars represent VEGF in normoxia; dark grey bars represent VEGF in hypoxia; white bars represent TSP1 in normoxia; black bars represent TSP1 in hypoxia. Results are normalized to the cyclophilin A mRNA level and expressed in arbitrary units, T0 set to 1.
Figure 4D:
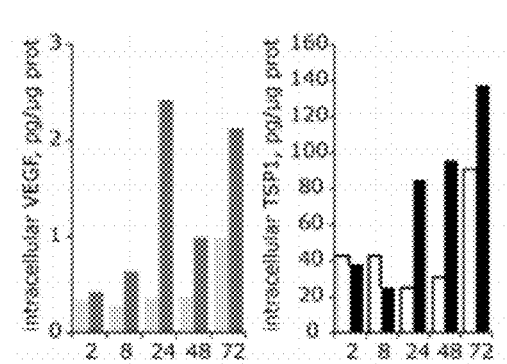
FIG. 4D represents VEGF and TSP1 protein content in C4-2 cell homogenates measured by ELISA and normalized to total protein content. Light grey bars represent VEGF in normoxia; dark grey bars represent Color code as in C.
Figure 4E:
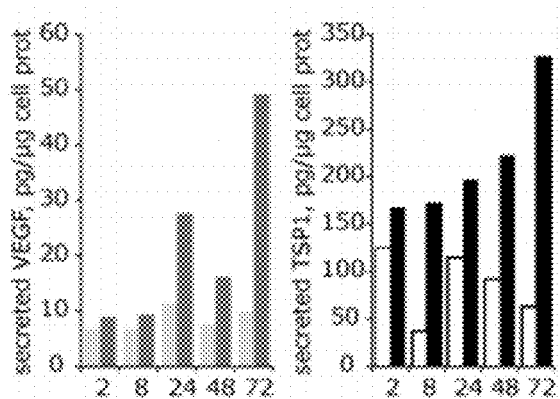
FIG. 4E represents VEGF and TSP1 protein content in C4-2 cell culture medium, measured by ELISA and normalized to total protein content in cell homogenates. Color code as in C.
Figure 4F:
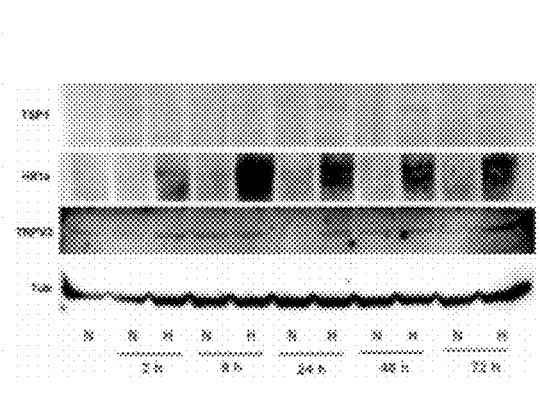
FIG. 4F represents TSP1, Hif1 alpha and TRPV3 protein content in C4-2 cell homogenates in cells grown for the indicated periods in normoxia (N) or hypoxia (H) Tubulin was used as a loading control.
Figure 4G:
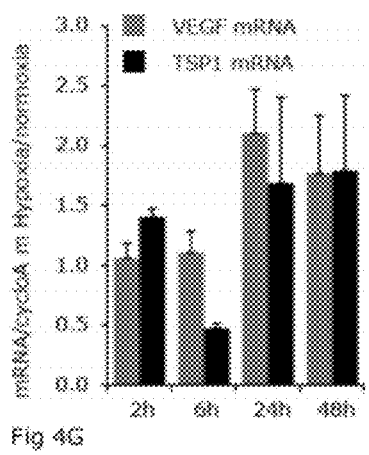
FIG. 4G represents the induction of VEGF (grey) and TSP1 (black) mRNA levels normalized to cyclophilin A levels in PC3 cells grown for the indicated periods in cobalt chloride as compared to the respective mRNA levels in control medium at the same time point.
Figure 4H:
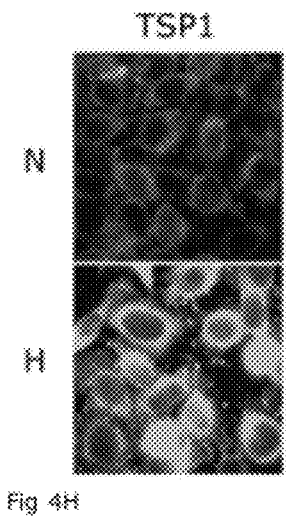
FIG. 4H represents TSP1 immunodetection in PC3 cells grown for 48 h in control conditions (N) or in the presence of 300 µM $CoCl_2$ to mimic hypoxia (H).

TSP1 is induced by hypoxia in human fibroblasts and vascular smooth muscle cells (Distler et al., 2007; Favier et al., 2005; Mayuko Osada-Oka, 2008). To analyze whether this was also the case in prostate tumor cells, C4-2 cells were grown in 1% or 20% oxygen, and VEGF and TSP1 expressions were compared at different time points up to 72 h. A time-dependent increase of both VEGF and TSP1 mRNA was observed in hypoxia at the mRNA (FIG. 4C) and protein level (FIG. 4D). As soon as 2 h after exposure to hypoxia, the secretion of TSP1 protein was induced (FIG. 4E). TRPV3 and Hif1 alpha proteins were also induced by hypoxia in a time-dependent manner (FIG. 4F). Similarly, exposure of PC3 cells to $CoCl_2$, which mimics the effects of hypoxia, induced TSP1 expressions at the mRNA (FIG. 4G) and protein levels (FIG. 4H).

Example 8

Figure 5A:
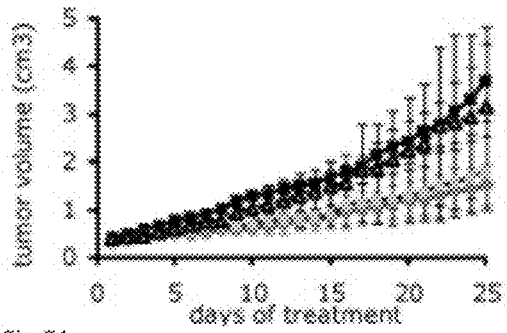
FIG. 5A represents tumor volume of mice bearing exponentially growing C4-2 tumors. Mice were treated daily with i.p. injections of PBS (triangles), Control-(black squares) TRPV3-(light grey diamonds) or TSP1-siRNA (dark grey diamonds). All siRNAs were diluted (120 µg/kg) in PBS. Tumor volume is expressed in $cm^3$ (mean±SEM, 6 mice per group).

In Vivo Silencing of TRPV3 or TSP1 Inhibits the Growth of Castration-Resistant or Androgen-Independent Prostate Tumors The In vitro data of the invention establish that the migration of C4-2 or PC3 cells is strongly impaired by TRPV3 or TSP1 silencing, without affecting cell proliferation or survival. In order to address the role of TSP1 and TRPV3 In vivo, C4-2 cells were xenografted into nude mice. Once tumors were exponentially growing, mice were randomized for treatment and received daily either PBS i.p. injections or 120 µg/kg of either control-, or TSP1-, or TRPV3-siRNA diluted into PBS and injected i.p. The growth of tumors in mice treated with TSP1- or TRPV3-siRNA was significantly inhibited (FIG. 5A). Similarly, both TRPV3- and TSP1-siRNAs inhibited the growth of xenografted PC3 tumors (FIG. 5B).

Figure 5B:
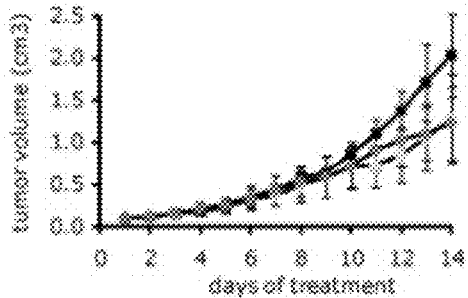
FIG. 5B represents tumor volume of mice bearing exponentially growing PC3 tumors. Mice were treated daily with i.p. injections of Control-(black squares) TRPV3-(light grey diamonds) or TSP1-siRNA (dark grey diamonds). All siRNAs were diluted (120 µg/kg) in PBS. Tumor volume is expressed in $cm^3$ (mean±SEM, 6 mice per group).
Figure 5C:
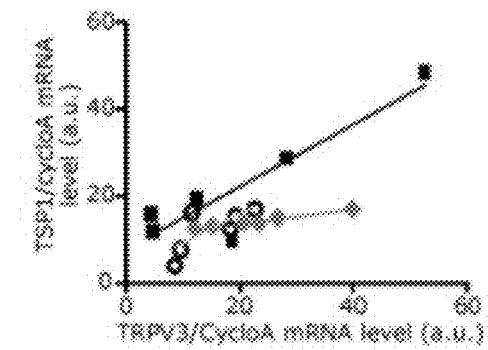
FIG. 5C represents TRPV3 and TSP1 mRNA levels, normalized to cyclophilin A and expressed in arbitrary units, in PC3 tumors collected at the end of the experiment depicted in FIG. 5B. The TSP1 mRNA level was plotted against the TRPV3 mRNA level in the same tumor from mice treated with control-siRNA (black squares), TRPV3-siRNA (grey diamonds) or TSP1-siRNA (white circles).

In control PC3 tumors collected at the end of the experiment depicted in FIG. 5B, a high degree of correlation was observed ($r^2=0.83$) between the TRPV3 and TSP1 mRNA levels (FIG. 5C). As compared to controls, treatment by TSP1-siRNA significantly decreased the TSP1 mRNA level in PC3 tumors (FIG. 5C). Of note, silencing TRPV3 resulted into a reduction of TRPV3 mRNA level, but also into a reduction of TSP1 mRNA level (FIG. 5C). These data confirm that, In vivo as In vitro, TRPV3 regulates TSP1 expression.

Figure 5D:
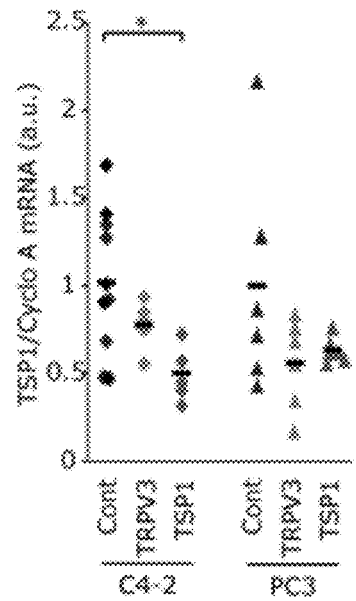
FIG. 5D represents the TSP1 mRNA level, normalized to cyclophilin A mRNA level, in tumors collected at the end of experiments shown in FIGS. 5A (C4-2, diamonds) and 5B (PC3, triangles). Tumors were treated by control-siRNA (black symbols), or TRPV3-siRNA (light grey symbols) or TSP1-siRNA (dark grey symbols).
Figure 5E:
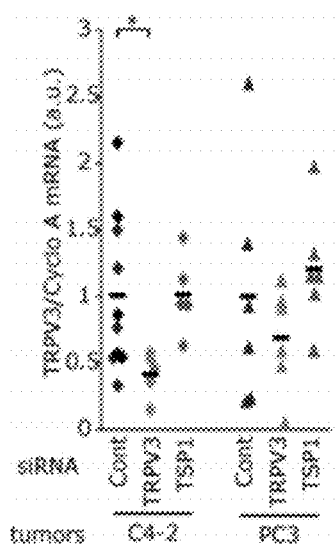
FIG. 5E represents the TRPV3 mRNA level, normalized to cyclophilin A mRNA level, in tumors collected at the end of experiments shown in FIGS. 4A (C4-2, diamonds) and 4B (PC3, triangles). Tumors were treated by control-siRNA (black symbols), or TRPV3-siRNA (light grey symbols) or TSP1-siRNA (dark grey symbols).

In C4-2 tumors, treatment by TRPV3- or TSP1-siRNA significantly decreased the corresponding target mRNA level as compared to controls (FIG. 5D, 5E).

Example 9

TSP1 Still Exerts Antiangiogenic Properties in Castration-Resistant Tumors

Figure 5F:
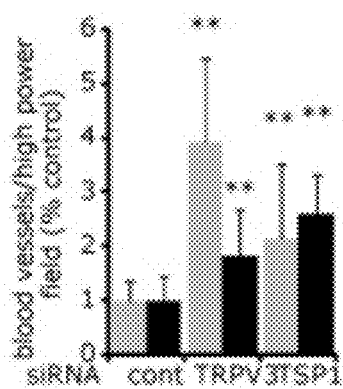
FIG. 5F represents the quantification of microvessel density (MVD) in hot spots of vascularization from C4-2 (grey bars) or PC3 (black bars) tumors collected at the end of the experiment described in FIG. 5A and FIG. 5B.
Figure 5G:
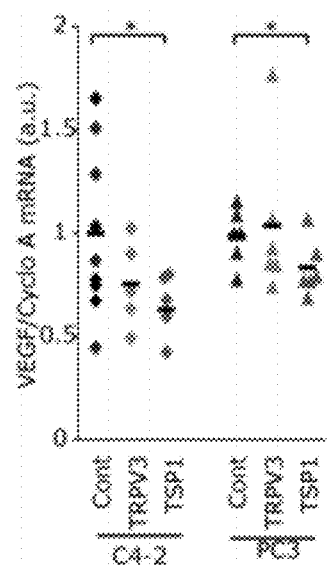
FIG. 5G represents the VEGF mRNA level, normalized to cyclophilin A mRNA level, in tumors collected at the end of experiments shown in FIGS. 4A (C4-2, diamonds) and 4B (PC3, triangles). Tumors were treated by control-siRNA (black symbols), or TRPV3-siRNA (light grey symbols) or TSP1-siRNA (dark grey symbols).

Although C4-2 and PC3 tumors treated by TSP1- or TRPV3-siRNA were smaller and highly necrotic, their microvessel blood density (MVD) in non-necrotic regions was significantly higher than in controls (FIG. 5F), showing that TSP1 still repressed angiogenesis in CRCaP and AICaP tumors. The increased MVD paralleled a reduced VEGF expression in TSP1-siRNA treated tumors (FIG. 5G), indicative of a reduced hypoxia. This result establishes that TSP1 still exerts antiangiogenic properties in C4-2 and PC3 tumors.

Example 10

Figure 5H:
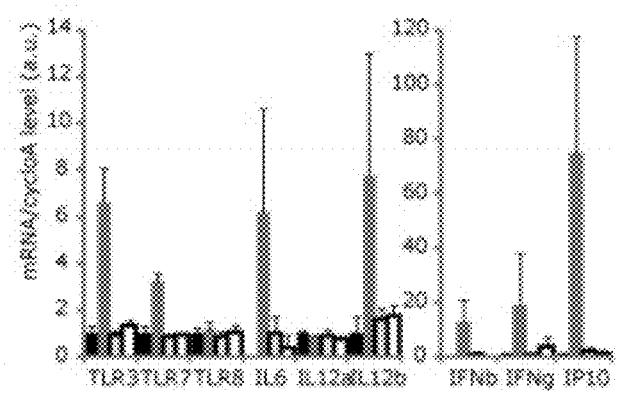
FIG. 5H represents mRNA level of the indicated genes in sacrificed nude mice 5 hours after an i.p. injection of PBS (black bars), or 4000 µg/kg of either poly(I:C), a known ligand of TLR3 (dark grey bars), or TRPV3b-siRNA (light grey bars) or TSP1a-siRNA (white bars) all diluted in PBS. The mRNA level of the indicated genes, normalized to cyclophilin A, was quantified by real time RT-PCR in the spleen. Results (mean±SEM, n=4) are expressed in arbitrary units, normalized to the value in PBS controls set to 1.

Absence of Induction of the Expression of Interferon or Inflammatory Cytokines In order to confirm that the antitumoral effects observed in vivo were not linked to a non-specific immune response, mice were given one injection by intraperitoneal route of TSP1a-siRNA, or of TRPV3b-siRNA, or of Poly (I:C), a known ligand of TLR3, used as a positive control. All the injections were carried out with a dose of 4 mg/kg siRNA diluted in PBS. Five hours after injection, mRNAs coding several genes involved in innate immune response or in inflammation were quantified by quantitative real time RT-PCT. Only the treatment by Poly (I:C) induces a significant increase of TLR3, TLR7, IL6, IL12b, IFNβ, IFNγ, and IP10, whereas neither TSP1-siRNA nor TRPV3-siRNA at the same dosage, 33 fold higher than that used in tumor experiments, induced these TLR and cytokines (FIG. 5H). These results establish that the antitumor effect observed by injections of TSP1-siRNA or TRPV3-siRNA in vivo cannot be attributed to a stimulation of innate immunity.

Example 11

TSP1 Expression is Associated with Pathological Stage and Cancer Recurrence after Radical Prostatectomy TSP1 mRNA expression was studied in 26 frozen radical prostatectomy specimens from patients with clinically localized prostate cancer who did not receive any radiotherapy and/or hormonal ablation treatment before surgery. Pairs of tumor and peritumoral tissue were analyzed in 18 specimens. The mean TSP1 mRNA level was significantly higher in peritumoral tissue than in tumors (Table 1), confirming that TSP1 expression is repressed in untreated androgen-dependent tumors.

Figure 6A:
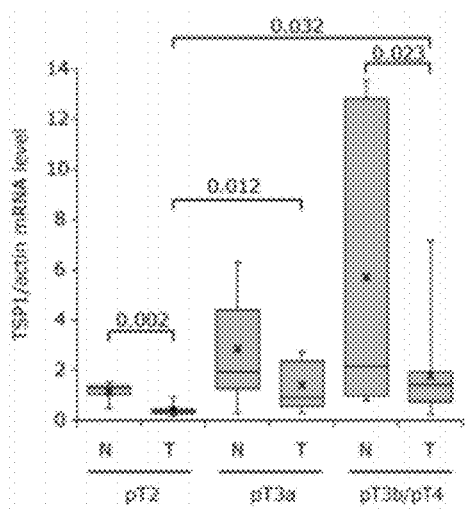
FIG. 6A represents TSP1 mRNA level, normalized to actin mRNA, in peritumoral (N) and tumoral (T) tissues from frozen radical prostatectomy samples of different clinical stages (pT2, pT3a, pT3b/pT4) taken before any other treatment. Each box plot is composed of three horizontal lines that display the 25th, 50th (median), and 75th percentiles. The highest and lowest values are shown using error bars. P value is shown when significant.

There was no significant association between tumoral or peritumoral TSP1 mRNA level and patients' age, Gleason score or serum PSA level before surgery (Table 1). In tumoral tissue, TSP1 mRNA level was significantly lower in patients with localized disease (pT2) as compared to those with locally advanced prostate cancer (pT3) (Table 1 and FIG. 6A). In peritumoral tissue, there is a trend towards higher TSP1 mRNA level in patients with higher stage disease although the difference was not statistically significant.

Figure 6B:
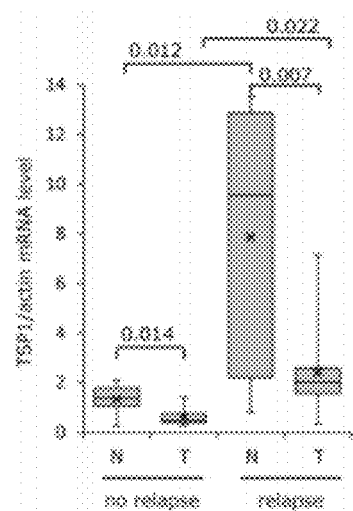
FIG. 6B represents the comparison of TSP1 mRNA level, normalized to actin mRNA, in samples from patients who did not show evidence of tumor recurrence during at least 30 months following surgery (n=8) or who experienced PSA relapse (n=11) after surgery.

Of the 26 patients included in this study, 11 experienced PSA relapse, whereas 8, followed for at least 30 months after surgery, did not show evidence of tumor recurrence. TSP1 mRNA level, measured in tumoral and peritumoral tissue at the time of radical prostatectomy, was significantly associated with PSA relapse (Table 1 and FIG. 6B).

TABLE 1

| | TSP1/actin mRNA level (a.u.) | | | | | | |
|---|---|---|---|---|---|---|---|
| | Peritumoral tissue (N) | | | Tumor (T) | | | |
| Criteria | No | Mean [range] | p | No | Mean [range] | p | p T vs N |
| All patients | 18 | 3.88 [0.26-13.54] | | 26 | 1.25 [0.20-7.15] | | 0.004 |
| age | | | | | | | |
| <=60 | 8 | 4.94 [0.49-13.54] | | 13 | 1.61 [0.20-7.15] | | 0.028 |
| >60 | 10 | 3.04 [0.26-12.81] | 0.197 | 13 | 0.90 [0.23-2.04] | 0.110 | 0.028 |
| Gleason score | | | | | | | |
| 6 | 2 | 0.53 [0.26-0.81] | | 6 | 1.15 [0.31-2.53] | | 0.191 |
| 7 | 13 | 4.70 [0.49-13.54] | 0.139+ | 15 | 1.31 [0.20-7.15] | 0.419+ | 0.011 |
| >7 | 3 | 2.58 [0.82-5.02] | 0.150+ | 5 | 1.20 [0.23-2.13] | 0.459+ | 0.118 |
| PSA before surgery (ng/ml) | | | | | | | |
| <7 | 6 | 5.01 [0.26-12.9] | | 10 | 1.64 [0.24-7.15] | | 0.063 |
| 7-15 | 6 | 1.27 [0.49-2.17] | 0.082° | 8 | 0.95 [0.20-2.53] | 0.195° | 0.219 |
| >15 | 5 | 5.44 [0.82-13.54] | 0.452° | 7 | 1.20 [0.28-2.60] | 0.306° | 0.025 |
| unknown | 1 | 5.02 | | 1 | 0.23 | | |
| stage | | | | | | | |
| pT2 | 4 | 1.15 [0.49-1.51] | | 8 | 0.41 [0.20-0.93] | | 0.002 |
| pT3a | 5 | 2.83 [0.26-6.31] | 0.114* | 7 | 1.40 [0.28-2.75] | 0.012* | 0.098 |
| pT3b | 8 | 5.77 [0.81-13.54] | 0.085* | 10 | 1.93 [0.33-7.15] | 0.023* | 0.039 |
| pT4 | 1 | 5.02 | | 1 | 0.23 | | |
| Tumor relapse (follow-up in months, mean [range]) | | | | | | | |
| no 51 [30-64] | 6 | 1.34 [0.26-2.10] | | 8 | 0.64 [0.30-1.41] | | 0.014 |
| yes 36 [6-80] | 7 | 7.46 [0.81-13.54] | 0.012 | 10 | 2.19 [0.23-7.15] | 0.022 | 0.007 |

REFERENCES

Abeele, F. V., Skryma, R., Shuba, Y., Van Coppenolle, F., Slomianny, C., Roudbaraki, M., Mauroy, B., Wuytack, F., and Prevarskaya, N. (2002). Bcl-2-dependent modulation of Ca2+ homeostasis and store-operated channels in prostate cancer cells. 1, 169-179.

Adams, J. C. (2004). Functions of the conserved thrombospondin carboxy-terminal cassette in cell-extracellular matrix interactions and signaling. The International Journal of Biochemistry & Cell Biology 36, 1102-1114.

Carlson, C. B., Lawler, J., and Mosher, D. F. (2008). Structures of thrombospondins. Cell Mol Life Sci 65, 672-686.

Carthew, R. W., and Sontheimer, E. J. (2009). Origins and Mechanisms of miRNAs and siRNAs. Cell 136, 642-655.

Colombel, M., Filleur, S., Fournier, P., Merle, C., Guglielmi, J., Courtin, A., Degeorges, A., Serre, C. M., Bouvier, R., Clezardin, P., and Cabon, F. (2005). Androgens repress the expression of the angiogenesis inhibitor thrombospondin-1 in normal and neoplastic prostate. Cancer Res 65, 300-308.

Filleur, S., Volpert, O. V., Degeorges, A., Voland, C., Reiher, F., Clezardin, P., Bouck, N., and Cabon, F. (2001). In vivo mechanisms by which tumors producing thrombospondin 1 bypass its inhibitory effects. Genes Dev 15, 1373-1382.

Fixemer, T., Wissenbach, U., Flockerzi, V., and Bonkhoff, H. (2003). Expression of the Ca2+-selective cation channel TRPV6 in human prostate cancer: a novel prognostic marker for tumor progression. Oncogene 22, 7858-7861.

Fontana, A., Filleur, S., Guglielmi, J., Frappart, L., Bruno-Bossio, G., Boissier, S., Cabon, F., and Clezardin, P. (2005a). Human breast tumors override the antiangiogenic effect of stromal thrombospondin-1 in vivo. Int J Cancer.

Fontana, A., Filleur, S., Guglielmi, J., Frappart, L., Bruno-Bossio, G., Boissier, S., Cabon, F., and Clézardin, P. (2005b). Human breast tumors override the antiangiogenic effect of stromal thrombospondin-1 in vivo. International Journal of Cancer 116, 686-691.

Good, D. J., Polyerini, P. J., Rastinejad, F., Le, B. M., Lemons, R. S., Frazier, W. A., and Bouck, N. P. (1990). A tumor suppressor-dependent inhibitor of angiogenesis is immunologically and functionally indistinguishable from a fragment of thrombospondin. Proc Natl Acad Sci USA 87, 6624-6628.

Grynkiewicz, G., Poenie, M., and Tsien, R. (1985). A new generation of Ca2+ indicators with greatly improved fluorescence properties. J Biol Chem 260, 3440-3450.

Jimenez, B., Volpert, O. V., Crawford, S. E., Febbraio, M., Silverstein, R. L., and Bouck, N. (2000). Signals leading to apoptosis-dependent inhibition of neovascularization by thrombospondin-1. Nat Med 6, 41-48.

Lehen'Kyi, V., Flourakis, M., Skryma, R., and Prevarskaya, N. (2007). TRPV6 channel controls prostate cancer cell proliferation via Ca2+//NFAT-dependent pathways. Oncogene 26, 7380-7385.

Li, Q., Ahuja, N., Burger, P. C., and Issa, J. P. (1999). Methylation and silencing of the Thrombospondin-1 promoter in human cancer. Oncogene 18, 3284-3289.

Mariot, P., Vanoverberghe, K., Lalevee, N., Rossier, M. F., and Prevarskaya, N. (2002). Overexpression of an alpha 1H (Cav3.2) T-type Calcium Channel during Neuroendocrine Differentiation of Human Prostate Cancer Cells. J Biol Chem 277, 10824-10833.

Monet, M., Lehen'kyi, V., Gackiere, F., Firlej, V., Vandenberghe, M., Roudbaraki, M., Gkika, D., Pourtier, A., Bidaux, G., Slomianny, C., et al. (2010). Role of cationic channel TRPV2 in promoting prostate cancer migration and progression to androgen resistance. Cancer Res 70, 1225-1235.

Moqrich, A., Hwang, S. W., Earley, T. J., Petrus, M. J., Murray, A. N., Spencer, K. S., Andahazy, M., Story, G. M., and Patapoutian, A. (2005). Impaired thermosensation in mice lacking TRPV3, a heat and camphor sensor in the skin. Science 307, 1468-1472.

Prevarskaya, N., Zhang, L., and Barritt, G. (2007). TRP channels in cancer. Biochimica et Biophysica Acta (BBA)—Molecular Basis of Disease 1772, 937-946.

Ren, B., Yee, K. O., Lawler, J., and Khosravi-Far, R. (2006). Regulation of tumor angiogenesis by thrombospondin-1. Biochimica et Biophysica Acta (BBA)—Reviews on Cancer 1765, 178-188.

Roberts, D. D. (2008). Thrombospondins: from structure to therapeutics. Cell Mol Life Sci 65, 669-671.

Sramkoski, R. M., Pretlow, T. G., 2nd, Giaconia, J. M., Pretlow, T. P., Schwartz, S., Sy, M. S., Marengo, S. R., Rhim, J. S., Zhang, D., and Jacobberger, J. W. (1999). A new human prostate carcinoma cell line, 22Rv1. In Vitro Cell Dev Biol Anim 35, 403-409.

Thalmann, G. N., Anezinis, P. E., Chang, S. M., Zhau, H. E., Kim, E. E., Hopwood, V. L., Pathak, S., von Eschenbach, A. C., and Chung, L. W. (1994). Androgen-independent cancer progression and bone metastasis in the LNCaP model of human prostate cancer. Cancer Res 54, 2577-2581.

Thebault, S., Flourakis, M., Vanoverberghe, K., Vandermoere, F., Roudbaraki, M., Lehen'kyi, V. y., Slomianny, C., Beck, B., Mariot, P., Bonnal, J.-L., et al. (2006). Differential Role of Transient Receptor Potential Channels in Ca2+ Entry and Proliferation of Prostate Cancer Epithelial Cells. Cancer Res 66, 2038-2047.

Vogt-Eisele, A. K., Weber, K., Sherkheli, M. A., Vielhaber, G., Panten, J., Gisselmann, G., and Hatt, H. (2007). Monoterpenoid agonists of TRPV3. Br J Pharmacol 151, 530-540.

Yuan, Y., Hilliard, G., Ferguson, T., and Millhorn, D. E. (2003). Cobalt Inhibits the Interaction between Hypoxia-inducible Factor-alpha and von Hippel-Lindau Protein by Direct Binding to Hypoxia-inducible Factor-alpha. J Biol Chem 278, 15911-15916.

Zhang, X., and Lawler, J. (2007). Thrombospondin-based antiangiogenic therapy. Microvasc Res 74, 90-99.

The invention claimed is:

1. A method for the treatment of prostate tumors, and breast tumors, comprising administering to a subject in need thereof an effective amount of a compound that inhibits the expression of or the activity of Thrombospondin-1 (TSP1), wherein the compound comprises:
- a double-stranded oligonucleotide comprising two oligonucleotide sequences, (a) and (b), forming a hybrid, wherein the oligonucleotide sequence (a)
  - is complementary to the oligonucleotide sequence (b), or presents less than 40% mismatches with said oligonucleotide sequence (b), and
  - is complementary to a target nucleotide sequence coding for the TSP1 protein, or presents less than 40% mismatches with said target sequence; or
- a fragment of the above-defined double-stranded oligonucleotide, comprising two complementary fragments of the respective above-defined oligonucleotide sequences (a) and (b), provided that said fragment conserves the property of inhibiting the expression of TSP1; or
- a double-stranded oligonucleotide comprising two oligonucleotide sequences, (a) and (b), forming a hybrid, wherein each oligonucleotide sequence comprises at one of its 3' or 5' ends, one to five unpaired nucleotides, forming single-stranded ends extending beyond the hybrid, wherein the hybrid portion of the oligonucleotide sequence (a)
  - is complementary to the oligonucleotide sequence (b), or presents less than 40% mismatches with said oligonucleotide sequence (b), and
  - is complementary to a target nucleotide sequence coding for the TSP1 protein, or presents less than 40% mismatches with said target sequence; or a fragment of the above-defined double-stranded oligonucleotide, comprising two complementary fragments of the respective above-defined oligonucleotide sequences (a) and (b), provided that said fragment conserves the property of inhibiting the expression of TSP1 one.

2. The method according to claim 1, wherein the compound inhibits the expression of TSP1.

3. The method according to claim 1, wherein the compound is a combination product administered simultaneously, separately, or spread over time, said combination product comprising:
   at least one of said double-stranded oligonucleotides, and an anti-angiogenic agent,
   at least one of said double-stranded oligonucleotides, and an anti-tumoral agent, or
   at least one of said double-stranded oligonucleotides, and an anti-angiogenic agent, and an anti-tumoral agent.

4. The method according to claim 1, wherein the compound is administered in combination with an anti-tumoral therapy, radiotherapy or chemotherapy.

5. The method according to claim 1, wherein the compound comprises a double-stranded oligonucleotide selected from the group consisting of:
   (SEQ ID NO: 1 and SEQ ID NO: 2);
   (SEQ ID NO: 3 and SEQ ID NO: 4);
   (SEQ ID NO: 21 and SEQ ID NO: 22);
   (SEQ ID NO: 23 and SEQ ID NO: 24);
   (SEQ ID NO: 5 and SEQ ID NO: 6);
   (SEQ ID NO: 7 and SEQ ID NO: 8);
   (SEQ ID NO: 25 and SEQ ID NO: 26); and
   (SEQ ID NO: 27 and SEQ ID NO: 28).

6. The method according to claim 5, wherein the double-stranded oligonucleotide is selected from the group consisting of:
   (SEQ ID NO: 1 and SEQ ID NO: 2);
   (SEQ ID NO: 3 and SEQ ID NO: 4);
   (SEQ ID NO: 21 and SEQ ID NO: 22); and
   (SEQ ID NO: 23 and SEQ ID NO: 24).

7. The method according to claim 1, wherein the compound is siRNA.

8. The method according to claim 1, wherein the oligonucleotide sequence (a) comprises zero mismatches with the oligonucleotide sequence (b).

9. The method according to claim 1, wherein the oligonucleotide sequence (a) comprises one mismatch with the oligonucleotide sequence (b).

10. The method according to claim 1, wherein the oligonucleotide sequence (a) comprises less than 20% mismatches with the oligonucleotide sequence (b).

11. A method for inhibiting cell migration in tumor development wherein TSP-1 is expressed, comprising contacting a TSP-1 expressing tumor cell with a composition comprising a double-stranded oligonucleotide selected from the group consisting of:
   (SEQ ID NO: 1 and SEQ ID NO: 2);
   (SEQ ID NO: 3 and SEQ ID NO: 4);
   (SEQ ID NO: 21 and SEQ ID NO: 22);
   (SEQ ID NO: 23 and SEQ ID NO: 24);
   (SEQ ID NO: 5 and SEQ ID NO: 6);
   (SEQ ID NO: 7 and SEQ ID NO: 8);
   (SEQ ID NO: 25 and SEQ ID NO: 26); and
   (SEQ ID NO: 27 and SEQ ID NO: 28).

12. The method according to claim 11, wherein the double-stranded oligonucleotide is selected from the group consisting of:
   (SEQ ID NO: 1 and SEQ ID NO: 2);
   (SEQ ID NO: 3 and SEQ ID NO: 4);
   (SEQ ID NO: 21 and SEQ ID NO: 22); and
   (SEQ ID NO: 23 and SEQ ID NO: 24).

13. A pharmaceutical composition, comprising at least one double-stranded oligonucleotide selected from the group consisting of:
   (SEQ ID NO: 1 and SEQ ID NO: 2);
   (SEQ ID NO: 3 and SEQ ID NO: 4);
   (SEQ ID NO: 21 and SEQ ID NO: 22); and
   (SEQ ID NO: 23 and SEQ ID NO: 24),
in association with a pharmaceutically acceptable vehicle.

14. The pharmaceutical composition according to claim 13, wherein the the at least one double stranded oligonucleotide is formulated for the administration to a subject at a dose in the range of 0.05 to 50 mg/kg.

15. The pharmaceutical composition according to claim 13, wherein the composition is a combination product for simultaneous, separate or spread over time use, said combination product comprising:
   the at least one double stranded oligonucleotide, and
   an anti-angiogenic agent, an anti-tumoral agent, or a combination thereof.

16. The pharmaceutical composition according to claim 15, wherein the anti-angiogenic agent is selected from the group consisting of Cilengitide, Vandetanib, Lenalidomide, Thalidomide, Arsenic Trioxide, Bevacizumab, anti-VEGFR-1, anti-VEGFR-2, anti-PDGFR, anti-FMS-FLT-3, and anti-TK1.

17. The pharmaceutical composition according to claim 15, wherein the anti-tumoral agent is selected from the group consisting of alkylating agents, Bendamustine, Temozolomide, Mechlorethamine, Cyclophosphamide, Carmustine, Cisplatine, Busulfan, Thiotepa, Decarbazine, anti-metabolite agents, Pentostatine, Methotrexate, Pemetrexed, Floxuridine, Fluorouracil, Cytaraine, Mercaptopurine, Thiguanine, cytotoxic antibiotics, Rubitecan, Mitomycine C, Daunorubicin, Doxorubicine, Bleomycin, Plicamycin, Mitoxantrone HCl, Oxaliplatine, plant derivatives, Vinorelbine, BMS 184476, Vincristine sulfate, Vinblastine, and Docetaxel taxol.

18. An isolated double-stranded oligonucleotide selected from the group consisting of:
   (SEQ ID NO: 1 and SEQ ID NO: 2);
   (SEQ ID NO: 3 and SEQ ID NO: 4);
   (SEQ ID NO: 21 and SEQ ID NO: 22); and
   (SEQ ID NO: 23 and SEQ ID NO: 24).

* * * * *

```
                        SEQUENCE LISTING

<160> NUMBER OF SEQ ID NOS: 44

<210> SEQ ID NO 1
<211> LENGTH: 21
<212> TYPE: DNA
<213> ORGANISM: Artificial Sequence
<220> FEATURE:
<223> OTHER INFORMATION: Derived from human genome

<400> SEQUENCE: 1
ccuugacaac aacguggugt t                                               21

<210> SEQ ID NO 2
<211> LENGTH: 21
<212> TYPE: DNA
<213> ORGANISM: Artificial Sequence
<220> FEATURE:
<223> OTHER INFORMATION: Derived from human genom

<400> SEQUENCE: 2
caccacguug uugucaaggt t                                               21

<210> SEQ ID NO 3
<211> LENGTH: 21
<212> TYPE: DNA
<213> ORGANISM: Artificial Sequence
<220> FEATURE:
<223> OTHER INFORMATION: Derived from human genom

<400> SEQUENCE: 3
uacccgagac gauuguaugt t                                               21

<210> SEQ ID NO 4
<211> LENGTH: 21
<212> TYPE: DNA
<213> ORGANISM: Artificial Sequence
<220> FEATURE:
<223> OTHER INFORMATION: Derived from human genom

<400> SEQUENCE: 4
cauacaaucg ucucgggaut t                                               21

<210> SEQ ID NO 5
```

```
<211> LENGTH: 21
<212> TYPE: DNA
<213> ORGANISM: Artificial Sequence
<220> FEATURE:
<223> OTHER INFORMATION: Derived from human genom

<400> SEQUENCE: 5
caaggagagc gaacgcauct t                                            21

<210> SEQ ID NO 6
<211> LENGTH: 21
<212> TYPE: DNA
<213> ORGANISM: Artificial Sequence
<220> FEATURE:
<223> OTHER INFORMATION: Derived from human genom

<400> SEQUENCE: 6
gaugcguucg cucuccuugt t                                            21

<210> SEQ ID NO 7
<211> LENGTH: 21
<212> TYPE: DNA
<213> ORGANISM: Artificial Sequence
<220> FEATURE:
<223> OTHER INFORMATION: Derived from human genom

<400> SEQUENCE: 7
auguacagcg ucaugaucct t                                            21

<210> SEQ ID NO 8
<211> LENGTH: 21
<212> TYPE: DNA
<213> ORGANISM: Artificial Sequence
<220> FEATURE:
<223> OTHER INFORMATION: Derived from human genom

<400> SEQUENCE: 8
ggaucaugac gcuguacaut t                                            21

<210> SEQ ID NO 9
<211> LENGTH: 21
<212> TYPE: DNA
<213> ORGANISM: Artificial Sequence
<220> FEATURE:
<223> OTHER INFORMATION: Derived from human genom

<400> SEQUENCE: 9
ucucugagcg cacuauucat t                                            21

<210> SEQ ID NO 10
<211> LENGTH: 21
<212> TYPE: DNA
<213> ORGANISM: Artificial Sequence
<220> FEATURE:
<223> OTHER INFORMATION: Derived from human genom

<400> SEQUENCE: 10
ugaauagugc gcucagagat t                                            21

<210> SEQ ID NO 11
<211> LENGTH: 21
<212> TYPE: DNA
<213> ORGANISM: Artificial Sequence
<220> FEATURE:
<223> OTHER INFORMATION: Derived from human genom

<400> SEQUENCE: 11
```

-continued uauuccguuc ggucaucuat t         21

<210> SEQ ID NO 12
<211> LENGTH: 21
<212> TYPE: DNA
<213> ORGANISM: Artificial Sequence
<220> FEATURE:
<223> OTHER INFORMATION: Derived from human genom

<400> SEQUENCE: 12
uagaugaccg aacggaauat t         21

<210> SEQ ID NO 13
<211> LENGTH: 21
<212> TYPE: DNA
<213> ORGANISM: Artificial Sequence
<220> FEATURE:
<223> OTHER INFORMATION: Derived from human genom

<400> SEQUENCE: 13
uacagacagu uuuggaucut t         21

<210> SEQ ID NO 14
<211> LENGTH: 21
<212> TYPE: DNA
<213> ORGANISM: Artificial Sequence
<220> FEATURE:
<223> OTHER INFORMATION: Derived from human genom

<400> SEQUENCE: 14
agauccaaaa cugucuguat t         21

<210> SEQ ID NO 15
<211> LENGTH: 21
<212> TYPE: DNA
<213> ORGANISM: Artificial Sequence
<220> FEATURE:
<223> OTHER INFORMATION: Derived from human genom

<400> SEQUENCE: 15
ggagaaucug cugaaggaut t         21

<210> SEQ ID NO 16
<211> LENGTH: 21
<212> TYPE: DNA
<213> ORGANISM: Artificial Sequence
<220> FEATURE:
<223> OTHER INFORMATION: Derived from human genom

<400> SEQUENCE: 16
auccuucagc agauucucct t         21

<210> SEQ ID NO 17
<211> LENGTH: 21
<212> TYPE: DNA
<213> ORGANISM: Artificial Sequence
<220> FEATURE:
<223> OTHER INFORMATION: Derived from human genom

<400> SEQUENCE: 17
uaagagucaa ccucaacuat t         21

<210> SEQ ID NO 18
<211> LENGTH: 21
<212> TYPE: DNA

```
<213> ORGANISM: Artificial Sequence
<220> FEATURE:
<223> OTHER INFORMATION: Derived from human genom

<400> SEQUENCE: 18
uaguugaggu ugacucuuat t                                              21

<210> SEQ ID NO 19
<211> LENGTH: 21
<212> TYPE: DNA
<213> ORGANISM: Artificial Sequence
<220> FEATURE:
<223> OTHER INFORMATION: Derived from human genom

<400> SEQUENCE: 19
ggaagacagg caagaucuct t                                              21

<210> SEQ ID NO 20
<211> LENGTH: 21
<212> TYPE: DNA
<213> ORGANISM: Artificial Sequence
<220> FEATURE:
<223> OTHER INFORMATION: Derived from human genom

<400> SEQUENCE: 20
gagaucuugc cugucuucct t                                              21

<210> SEQ ID NO 21
<211> LENGTH: 19
<212> TYPE: DNA
<213> ORGANISM: Artificial Sequence
<220> FEATURE:
<223> OTHER INFORMATION: Derived from human genom

<400> SEQUENCE: 21
ccuugacaac aacguggug                                                 19

<210> SEQ ID NO 22
<211> LENGTH: 19
<212> TYPE: DNA
<213> ORGANISM: Artificial Sequence
<220> FEATURE:
<223> OTHER INFORMATION: Derived from human genom

<400> SEQUENCE: 22
caccacguug uugucaagg                                                 19

<210> SEQ ID NO 23
<211> LENGTH: 19
<212> TYPE: DNA
<213> ORGANISM: Artificial Sequence
<220> FEATURE:
<223> OTHER INFORMATION: Derived from human genom

<400> SEQUENCE: 23
uacccgagac gauuguaug                                                 19

<210> SEQ ID NO 24
<211> LENGTH: 19
<212> TYPE: DNA
<213> ORGANISM: Artificial Sequence
<220> FEATURE:
<223> OTHER INFORMATION: Derived from human genom

<400> SEQUENCE: 24
cauacaaucg ucucgggua                                                 19
```

<210> SEQ ID NO 25
<211> LENGTH: 19
<212> TYPE: DNA
<213> ORGANISM: Artificial Sequence
<220> FEATURE:
<223> OTHER INFORMATION: Derived from human genom

<400> SEQUENCE: 25
caaggagagc gaacgcauc                                                    19

<210> SEQ ID NO 26
<211> LENGTH: 19
<212> TYPE: DNA
<213> ORGANISM: Artificial Sequence
<220> FEATURE:
<223> OTHER INFORMATION: Derived from human genom

<400> SEQUENCE: 26
gaugcguucg cucuccuug                                                    19

<210> SEQ ID NO 27
<211> LENGTH: 19
<212> TYPE: DNA
<213> ORGANISM: Artificial Sequence
<220> FEATURE:
<223> OTHER INFORMATION: Derived from human genom

<400> SEQUENCE: 27
auguacagcg ucaugaucc                                                    19

<210> SEQ ID NO 28
<211> LENGTH: 19
<212> TYPE: DNA
<213> ORGANISM: Artificial Sequence
<220> FEATURE:
<223> OTHER INFORMATION: Derived from human genom

<400> SEQUENCE: 28
ggaucaugac gcuguacau                                                    19

<210> SEQ ID NO 29
<211> LENGTH: 19
<212> TYPE: DNA
<213> ORGANISM: Artificial Sequence
<220> FEATURE:
<223> OTHER INFORMATION: Derived from human genom

<400> SEQUENCE: 29
ucucugagcg cacuauuca                                                    19

<210> SEQ ID NO 30
<211> LENGTH: 19
<212> TYPE: DNA
<213> ORGANISM: Artificial Sequence
<220> FEATURE:
<223> OTHER INFORMATION: Derived from human genom

<400> SEQUENCE: 30
ugaauagugc gcucagaga                                                    19

<210> SEQ ID NO 31
<211> LENGTH: 19
<212> TYPE: DNA
<213> ORGANISM: Artificial Sequence
<220> FEATURE:

```
<223> OTHER INFORMATION: Derived from human genom

<400> SEQUENCE: 31
uauuccguuc ggucaucua                                              19

<210> SEQ ID NO 32
<211> LENGTH: 19
<212> TYPE: DNA
<213> ORGANISM: Artificial Sequence
<220> FEATURE:
<223> OTHER INFORMATION: Derived from human genom

<400> SEQUENCE: 32
uagaugaccg aacggaaua                                              19

<210> SEQ ID NO 33
<211> LENGTH: 19
<212> TYPE: DNA
<213> ORGANISM: Artificial Sequence
<220> FEATURE:
<223> OTHER INFORMATION: Derived from human genom

<400> SEQUENCE: 33
uacagacagu uuuggaucu                                              19

<210> SEQ ID NO 34
<211> LENGTH: 19
<212> TYPE: DNA
<213> ORGANISM: Artificial Sequence
<220> FEATURE:
<223> OTHER INFORMATION: Derived from human genom

<400> SEQUENCE: 34
agauccaaaa cugucugua                                              19

<210> SEQ ID NO 35
<211> LENGTH: 19
<212> TYPE: DNA
<213> ORGANISM: Artificial Sequence
<220> FEATURE:
<223> OTHER INFORMATION: Derived from human genom

<400> SEQUENCE: 35
ggagaaucug cugaaggau                                              19

<210> SEQ ID NO 36
<211> LENGTH: 19
<212> TYPE: DNA
<213> ORGANISM: Artificial Sequence
<220> FEATURE:
<223> OTHER INFORMATION: Derived from human genom

<400> SEQUENCE: 36
auccuucagc agauucucc                                              19

<210> SEQ ID NO 37
<211> LENGTH: 19
<212> TYPE: DNA
<213> ORGANISM: Artificial Sequence
<220> FEATURE:
<223> OTHER INFORMATION: Derived from human genom

<400> SEQUENCE: 37
uaagagucaa ccucaacua                                              19
```

-continued

```
<210> SEQ ID NO 38
<211> LENGTH: 19
<212> TYPE: DNA
<213> ORGANISM: Artificial Sequence
<220> FEATURE:
<223> OTHER INFORMATION: Derived from human genom

<400> SEQUENCE: 38
uaguugaggu ugacucuua                                                 19

<210> SEQ ID NO 39
<211> LENGTH: 19
<212> TYPE: DNA
<213> ORGANISM: Artificial Sequence
<220> FEATURE:
<223> OTHER INFORMATION: Derived from human genom

<400> SEQUENCE: 39
ggaagacagg caagaucuc                                                 19

<210> SEQ ID NO 40
<211> LENGTH: 19
<212> TYPE: DNA
<213> ORGANISM: Artificial Sequence
<220> FEATURE:
<223> OTHER INFORMATION: Derived from human genom

<400> SEQUENCE: 40
gagaucuugc cugucuucc                                                 19

<210> SEQ ID NO 41
<211> LENGTH: 5820
<212> TYPE: DNA
<213> ORGANISM: Homo sapiens

<400> SEQUENCE: 41
agccgctgcg cccgagctgg cctgcgagtt cagggctcct gtcgctctcc aggagcaacc     60
tctactccgg acgcacaggc attccccgcg cccctccagc cctcgccgcc ctcgccaccg    120
ctcccggccg ccgcgctccg gtacacacag gatccctgct gggcaccaac agctccacca    180
tggggctggc ctggggacta ggcgtcctgt tcctgatgca tgtgtgtggc accaaccgca    240
ttccagagtc tggcgagac aacagcgtgt tgacatctt tgaactcacc ggggccgccc     300 gcaagggtc tgggcgccga ctggtgaagg ccccgaccc ttccagccca gctttccgca    360
tcgaggatgc caacctgatc ccccctgtgc ctgatgacaa gttccaagac tggtggatg    420 ctgtgcgggc agaaaagggt ttcctccttc tggcatccct gaggcagatg aagaagaccc    480
ggggcacgct gctggccctg agcggaaag accactctgg ccaggtcttc agcgtggtgt    540
ccaatggcaa ggcgggcacc ctggacctca gcctgaccgt ccaaggaaag cagcacgtgg    600
tgtctgtgga agaagctctc ctggcaaccg gccagtggaa gagcatcacc ctgtttgtgc    660
aggaagacag ggcccagctg tacatcgact gtgaaaagat ggagaatgct gagttggacg    720
tccccatcca agcgtcttc accagagacc tggccagcat cgccagactc cgcatcgcaa    780 agggggcgt caatgacaat ttccaggggg tgctgcagaa tgtgaggttt gtctttggaa    840
ccacaccaga agacatcctc aggaacaaag gctgctccag ctctaccagt gtcctcctca    900
cccttgacaa caacgtggtg aatggttcca gccctgccat ccgcactaac tacattggcc    960
acaagacaaa ggacttgcaa gccatctgcg gcatctcctg tgatgagctg tccagcatgg   1020
tcctggaact caggggcctg cgcaccattg tgaccacgct gcaggacagc atccgcaaag   1080
```

```
tgactgaaga gaacaaagag ttggccaatg agctgaggcg gcctccccta tgctatcaca    1140
acggagttca gtacagaaat aacgaggaat ggactgttga tagctgcact gagtgtcact    1200
gtcagaactc agttaccatc tgcaaaaagg tgtcctgccc catcatgccc tgctccaatg    1260
ccacagttcc tgatggagaa tgctgtcctc gctgttggcc cagcgactct gcggacgatg    1320
gctggtctcc atggtccgag tggacctcct gttctacgag ctgtggcaat ggaattcagc    1380
agcgcggccg ctcctgcgat agcctcaaca accgatgtga gggctcctcg gtccagacac    1440
ggacctgcca cattcaggag tgtgacaaga gatttaaaca ggatggtggc tggagccact    1500 ggtcccgtg gtcatcttgt tctgtgacat gtggtgatgg tgtgatcaca aggatccggc    1560
tctgcaactc tcccagcccc cagatgaacg ggaaaccctg tgaaggcgaa gcgcgggaga    1620
ccaaagcctg caagaaagac gcctgcccca tcaatggagg ctggggtcct tggtcaccat    1680
gggacatctg ttctgtcacc tgtggaggag gggtacagaa acgtagtcgt ctctgcaaca    1740
accccacacc ccagtttgga ggcaaggact gcgttggtga tgtaacagaa aaccagatct    1800
gcaacaagca ggactgtcca attgatggat gcctgtccaa tccctgcttt gcggcgtga    1860 agtgtactag ctaccctgat ggcagctgga atgtggtgc ttgtcccct ggttacagtg    1920 gaaatggcat ccagtgcaca gatgttgatg agtgcaaaga agtgcctgat gcctgcttca    1980
accacaatgg agagcaccgg tgtgagaaca cggaccccgg ctacaactgc ctgccctgcc    2040
ccccacgctt caccggctca cagcccttcg gccagggtgt cgaacatgcc acggccaaca    2100
aacaggtgtg caagccccgt aacccctgca cggatgggac ccacgactgc aacaagaacg    2160
ccaagtgcaa ctacctgggc cactatagcg accccatgta ccgctgcgag tgcaagcctg    2220
gctacgctgg caatggcatc atctgcgggg aggacacaga cctggatggc tggcccaatg    2280
agaacctggt gtgcgtggcc aatgcgactt accactgcaa aaaggataat tgccccaacc    2340
ttcccaactc agggcaggaa gactatgaca aggatggaat tggtgatgcc tgtgatgatg    2400
acgatgacaa tgataaaatt ccagatgaca gggacaactg tccattccat tacaacccag    2460
ctcagtatga ctatgacaga gatgatgtgg agaccgctg tgacaactgt ccctacaacc    2520
acaacccaga tcaggcagac acagacaaca atgggggaagg agacgcctgt gctgcagaca    2580
ttgatggaga cggtatcctc aatgaacggg acaactgcca gtacgtctac aatgtggacc    2640
agagagacac tgtatggat ggggttggag atcagtgtga caattgcccc ttggaacaca    2700
atccggatca gctggactct gactcagacc gcattggaga tacctgtgac aacaatcagg    2760
atattgatga agatggccac cagaacaatc tggacaactg tccctatgtg cccaatgcca    2820
accaggctga ccatgacaaa gatggcaagg agatgcctg tgaccacgat gatgacaacg    2880
atggcattcc tgatgacaag gacaactgca gactcgtgcc caatcccgac cagaaggact    2940
ctgacggcga tggtcgaggt gatgcctgca agatgatttt tgaccatgac agtgtgccag    3000
acatcgatga catctgtcct gagaatgttg acatcagtga gaccgatttc gccgattcc    3060 agatgattcc tctggacccc aaagggacat cccaaaatga ccctaactgg gttgtacgcc    3120
atcagggtaa agaactcgtc cagactgtca actgtgatcc tggactcgct gtaggttatg    3180
atgagtttaa tgctgtggac ttcagtgca ccttcttcat caacaccgaa agggacgatg    3240
actatgctgg atttgtcttt ggctaccagt ccagcagccg ctttttatgtt gtgatgtgga    3300 agcaagtcac ccagtcctac tgggacacca accccacgag ggctcaggga tactcgggcc    3360
tttctgtgaa agttgtaaac tccaccacag ggcctggcga gcacctgcgg aacgccctgt    3420
ggcacacagg aaacacccct ggccaggtgc gcaccctgtg gcatgaccct cgtcacatag    3480
```

```
gctggaaaga tttcaccgcc tacagatggc gtctcagcca caggccaaag acgggtttca   3540
ttagagtggt gatgtatgaa gggaagaaaa tcatggctga ctcaggaccc atctatgata   3600
aaacctatgc tggtggtaga ctagggttgt ttgtcttctc tcaagaaatg gtgttcttct   3660
ctgacctgaa atacgaatgt agagatccct aatcatcaaa ttgttgattg aaagactgat   3720
cataaaccaa tgctggtatt gcaccttctg gaactatggg cttgagaaaa ccccaggat    3780 cacttctcct tggcttcctt cttttctgtg cttgcatcag tgtggactcc tagaacgtgc   3840
gacctgcctc aagaaaatgc agttttcaaa acagactca  gcattcagcc tccaatgaat   3900 aagcatctt  ccaagcatat aaacaattgc tttggtttcc ttttgaaaaa gcatctactt   3960
gcttcagttg ggaaggtgcc cattccactc tgcctttgtc acagagcagg gtgctattgt   4020
gaggccatct ctgagcagtg gactcaaaag cattttcagg catgtcagag aagggaggac   4080
tcactagaat tagcaaacaa aaccaccctg acatcctcct tcaggaacac ggggagcaga   4140
ggccaaagca ctaaggggag ggcgcatacc cgagacgatt gtatgaagaa aatatggagg   4200
aactgttaca tgttcggtac taagtcattt tcaggggatt gaaagactat tgctggattt   4260
catgatgctg actggcgtta gctgattaac ccatgtaaat aggcacttaa atagaagcag   4320
gaaagggaga caaagactgg cttctggact tcctcccctga tccccaccct tactcatcac   4380
ctgcagtggc cagaattagg gaatcagaat caaaccagtg taaggcagtg ctggctgcca   4440
ttgcctggtc acattgaaat tggtggcttc attctagatg tagcttgtgc agatgtagca   4500
ggaaaatagg aaaacctacc atctcagtga gcaccagctg cctcccaaag gaggggcagc   4560
cgtgcttata ttttatggt  tacaatggca caaaattatt atcaacctaa ctaaaacatt   4620 cctttctct  tttttcctga attatcatgg agttttctaa ttctctcttt tggaatgtag   4680
atttttttta aatgctttac gatgtaaaat atttattttt tacttattct ggaagatctg   4740
gctgaaggat tattcatgga acaggaagaa gcgtaaagac tatccatgtc atctttgttg   4800
agagtcttcg tgactgtaag attgtaaata cagattattt attaactctg ttctgcctgg   4860
aaatttaggc ttcatacgga aagtgtttga gagcaagtag ttgacattta tcagcaaatc   4920
tcttgcaaga acagcacaag gaaaatcagt ctaataagct gctctgcccc ttgtgctcag   4980
agtggatgtt atgggattct ttttttctct gttttatctt ttcaagtgga attagttggt   5040
tatccatttg caaatgtttt aaattgcaaa gaaagccatg aggtcttcaa tactgttta   5100 ccccatccct tgtgcatatt tccagggaga aggaaagcat atacactttt ttctttcatt   5160
tttccaaaag agaaaaaat  gacaaaaggt gaaacttaca tacaaatatt acctcatttg   5220
ttgtgtgact gagtaaagaa ttttggatc  aagcggaaag agtttaagtg tctaacaaac   5280
ttaaagctac tgtagtacct aaaaagtcag tgttgtacat agcataaaaa ctctgcagag   5340
aagtattccc aataaggaaa tagcattgaa atgttaaata caattctga  aagttatgtt   5400 tttttttctat catctggtat accattgctt tattttata  aattattttc tcattgccat   5460
tggaatagat atctcagatt gtgtagatat gctatttaaa taatttatca ggaaatactg   5520
cctgtagagt tagtatttct attttttatat aatgtttgca cactgaattg aagaattgtt   5580
ggttttttct tttttttgtt ttgtttttt  ttttttttt  ttttgctttt gacctcccat   5640
ttttactatt tgccaatacc tttttctagg aatgtgcttt ttttttgtaca cattttatc    5700 cattttcat  tctaaagcag tgtaagttgt atattactgt ttcttatgta caaggaacaa   5760
caataaatca tatggaaatt tatatttata aaaaaaaaa  aaaaaaaa   aaaaaaaaa    5820
```

<210> SEQ ID NO 42
<211> LENGTH: 3162
<212> TYPE: DNA
<213> ORGANISM: Homo sapiens

<400> SEQUENCE: 42

| | | | | | |
|---|---|---|---|---|---|
| gggccccaga | catgcggtga | tctcagggca | agggttgcca | cgaccaccca | gaacctcacc | 60 |
| agccatgaaa | gcccacccca | aggagatggt | gcctctcatg | ggcaagagag | ttgctgcccc | 120 |
| cagtgggaac | cctgccatcc | tgccagagaa | gaggccggcg | gagatcaccc | ccacaaagaa | 180 |
| gagtgcacac | ttcttcctgg | agatagaagg | gtttgaaccc | aacccacag | ttgccaagac | 240 |
| ctctcctcct | gtcttctcca | agcccatgga | ttccaacatc | cggcagtgca | tctctggtaa | 300 |
| ctgtgatgac | atggactccc | cccagtctcc | tcaggatgat | gtgacagaga | ccccatccaa | 360 |
| tcccaacagc | cccagtgcac | agctggccaa | ggaagagcag | aggaggaaaa | agaggcggct | 420 |
| gaagaagcgc | atctttgcag | ccgtgtctga | gggctgcgtg | gaggagttgg | tagagttgct | 480 |
| ggtggagctg | caggagcttt | gcaggcggcg | ccatgatgag | gatgtgcctg | acttcctcat | 540 |
| gcacaagctg | acggcctccg | acacggggaa | gacctgcctg | atgaaggcct | tgttaaacat | 600 |
| caaccccaac | accaaggaga | tagtgcggat | cctgcttgcc | tttgctgaag | agaacgacat | 660 |
| cctgggcagg | ttcatcaacg | ccgagtacac | agaggaggcc | tatgaagggc | agacggcgct | 720 |
| gaacatcgcc | atcgagcggc | ggcaggggga | catcgcagcc | ctgctcatcg | ccgccggcgc | 780 |
| cgacgtcaac | gcgcacgcca | ggggggcctt | cttcaacccc | aagtaccaac | acgaaggctt | 840 |
| ctacttcggt | gagacgcccc | tggccctggc | agcatgcacc | aaccagcccg | agattgtgca | 900 |
| gctgctgatg | gagcacgagc | agacggacat | cacctcgcgg | gactcacgag | gcaacaacat | 960 |
| ccttcacgcc | ctggtgaccg | tggccgagga | cttcaagacg | cagaatgact | ttgtgaagcg | 1020 |
| catgtacgac | atgatcctac | tgcggagtgg | caactgggag | ctggagacca | tcgcaacaa | 1080 |
| cgatggcctc | acgccgctgc | agctggccgc | caagatgggc | aaggcggaga | tcctgaagta | 1140 |
| catcctcagt | cgtgagatca | aggagaagcg | gctccggagc | ctgtccagga | agttcaccga | 1200 |
| ctgggcgtac | ggaccgtgt | catcctcct | ctacgacctc | accaacgtgg | acaccaccac | 1260 |
| ggacaactca | gtgctggaaa | tcactgtcta | caacaccaac | atcgacaacc | ggcatgagat | 1320 |
| gctgaccctg | gagccgctgc | acacgctgct | gcatatgaag | tggaagaagt | ttgccaagca | 1380 |
| catgttcttt | ctgtccttct | gcttttattt | cttctacaac | atcaccctga | ccctcgtctc | 1440 |
| gtactaccgc | ccccgggagg | aggaggccat | cccgcacccc | ttggccctga | cgcacaagat | 1500 |
| ggggtggctg | cagctcctag | ggaggatgtt | tgtgctcatc | tgggccatgt | gcatctctgt | 1560 |
| gaaagagggc | attgccatct | tcctgctgag | accctcggat | ctgcagtcca | tcctctcgga | 1620 |
| tgcctggttc | cactttgtct | tttttatcca | agctgtgctt | gtgatactgt | ctgtcttctt | 1680 |
| gtacttgttt | gcctacaaag | agtacctcgc | ctgcctcgtg | ctggccatgg | ccctgggctg | 1740 |
| ggcgaacatg | ctctactata | cgcggggttt | ccagtccatg | gcatgtaca | gcgtcatgat | 1800 |
| ccagaaggtc | attttgcatg | atgttctgaa | gttcttgttt | gtatatatcg | tgttttttgct | 1860 |
| tggatttgga | gtagccttgg | cctcgctgat | cgagaagtgt | cccaaagaca | caaggactg | 1920 |
| cagctcctac | ggcagcttca | gcgacgcagt | gctggaactc | ttcaagctca | ccataggcct | 1980 |
| gggtgacctg | aacatccagc | agaactccaa | gtatccatt | ctctttctgt | tcctgctcat | 2040 |
| cacctatgtc | atcctcacct | tgttctcct | cctcaacatg | ctcattgctc | tgatgggcga | 2100 |
| gactgtggag | aacgtctcca | aggagagcga | acgcatctgg | cgcctgcaga | gagccaggac | 2160 |

```
catcttggag tttgagaaaa tgttaccaga atggctgagg agcagattcc ggatgggaga    2220
gctgtgcaaa gtggccgagg atgatttccg actgtgtttg cggatcaatg aggtgaagtg    2280
gactgaatgg aagacgcacg tctccttcct taacgaagac ccggggcctg taagacgaac    2340
agatttcaac aaaatccaag attcttccag gaacaacagc aaaaccactc tcaatgcatt    2400
tgaagaagtc gaggaattcc cggaaacctc ggtgtagaag cggaacccag agctggtgtg    2460
cgcgtgcgct gtctggcgct gcaggcggag tcaccgactc tgtgcagaga ggctttgagg    2520
gatggtggag tccggctctg ctggcctaga agcagagtgc accctcgtgc tcagtgctca    2580
gtgggtgtct gaactgaggg gcagttgtca atttgtctga gtgggaaaca tcctggattt    2640
tgttacttgg caaacagctg gtgtaaacct acagccagca gcagtctgga gcctgggagc    2700
ctcctgaagt cccgggtgaa gcctctggtt ttaccaattg caggtcggct tggctggag    2760 agatggatgg cgggaaaggg gcagcagtct tgaggagcag ggagaggagt ctttcctcct    2820
gccagcttcc cccgtcagcc ccaacccag cccacacatt gtaccatctc ttctgctgtg    2880
actgggttgc ctgaatttgt gggagacccg tgatcccatc ccagagtgtg cggggacgg    2940 aggtaagctg gatatcctgg gggaggaggg gaatgcgctc tggaaacacc cttccggaac    3000
ccttcgggga aaaggagacc atccttggag tgaacgtccc ctgacacccc aaggttcaaa    3060
ctgtctcaag ctgagagatg tttttagtag cagaattaac acagggtttt aacttgcaat    3120
acggaaaaga catttcagtt gagaatgaaa attactacaa tg                      3162

<210> SEQ ID NO 43
<211> LENGTH: 23
<212> TYPE: DNA
<213> ORGANISM: Artificial Sequence
<220> FEATURE:
<223> OTHER INFORMATION: Derived from human genome

<400> SEQUENCE: 43
gauagcaaug acgaaugcgu att                                            23

<210> SEQ ID NO 44
<211> LENGTH: 23
<212> TYPE: DNA
<213> ORGANISM: Artificial Sequence
<220> FEATURE:
<223> OTHER INFORMATION: Derived from human genome

<400> SEQUENCE: 44
uacgcauucg ucauugcuau ctt                                            23
```